United States Patent
Brannan et al.

(10) Patent No.: US 9,161,814 B2
(45) Date of Patent: Oct. 20, 2015

(54) MICROWAVE ENERGY-DELIVERY DEVICE AND SYSTEM

(71) Applicant: Covidien LP, Mansfield, MA (US)

(72) Inventors: Joseph D. Brannan, Erie, CO (US);
Casey M. Ladtkow, Erie, CO (US);
Darion R. Peterson, Boulder, CO (US);
Eric W. Larson, Thornton, CO (US);
William J. Dickhans, Longmont, CO (US); Richard A. Willyard, Longmont, CO (US); Jason A. Case, Longmont, CO (US)

(73) Assignee: Covidien LP, Mansfield, MA (US)

( * ) Notice: Subject to any disclaimer, the term of this patent is extended or adjusted under 35 U.S.C. 154(b) by 208 days.

(21) Appl. No.: 13/838,238

(22) Filed: Mar. 15, 2013

(65) Prior Publication Data
US 2014/0259641 A1    Sep. 18, 2014

(51) Int. Cl.
*H01F 7/06* (2006.01)
*A61B 18/04* (2006.01)
*A61B 18/18* (2006.01)
*A61B 18/00* (2006.01)

(52) U.S. Cl.
CPC ... *A61B 18/1815* (2013.01); *A61B 2018/00023* (2013.01); *A61B 2018/00166* (2013.01); *A61B 2018/00494* (2013.01); *A61B 2018/00511* (2013.01); *A61B 2018/00529* (2013.01); *A61B 2018/00577* (2013.01); *A61B 2018/00708* (2013.01); *A61B 2018/00797* (2013.01); *A61B 2018/00821* (2013.01); *A61B 2018/1861* (2013.01); *Y10T 29/4902* (2015.01)

(58) Field of Classification Search
CPC ............ H01F 17/0013; A61B 18/1815
USPC .............................. 29/602.1; 606/33
See application file for complete search history.

(56) References Cited

U.S. PATENT DOCUMENTS

| | | | | |
|---|---|---|---|---|
| 5,342,357 | A | * | 8/1994 | Nardella ................... 606/40 |
| 5,364,392 | A | * | 11/1994 | Warner et al. ............. 606/34 |
| 5,685,839 | A | * | 11/1997 | Edwards et al. .......... 604/22 |
| 6,239,724 | B1 | * | 5/2001 | Doron et al. ......... 340/870.28 |

(Continued)

FOREIGN PATENT DOCUMENTS

| | | |
|---|---|---|
| JP | 2001518351 A | 10/2001 |
| JP | 2011516184 A | 5/2011 |

(Continued)

OTHER PUBLICATIONS

European Search Report, Application No. EP 14 16 0251 dated Sep. 25, 2014.

(Continued)

*Primary Examiner* — David Angwin

(57) ABSTRACT

A method of manufacturing a microwave ablation device, the method including applying a balun short circumferentially about an outer conductor of a coaxial feedline and applying a dielectric material circumferentially about the outer conductor of the coaxial feedline and in contact with the balun short to form a balun. The method further including extending a temperature sensor along the coaxial feedline such that the sensor contacts the balun short, securing the temperature sensor to the coaxial feedline with a first heat shrink material, and securing the dielectric material, balun short, and temperature sensor in contact with each other and to the coaxial feedline using a second heat shrink material.

15 Claims, 20 Drawing Sheets

(56) References Cited

U.S. PATENT DOCUMENTS

| | | | |
|---|---|---|---|
| 6,419,680 B1* | 7/2002 | Cosman et al. | 606/130 |
| 6,427,089 B1* | 7/2002 | Knowlton | 607/101 |
| 6,575,969 B1* | 6/2003 | Rittman et al. | 606/41 |
| 6,689,127 B1* | 2/2004 | Gough et al. | 606/41 |
| 7,047,063 B2* | 5/2006 | Burbank et al. | 600/431 |
| 7,294,127 B2* | 11/2007 | Leung et al. | 606/41 |
| 7,783,336 B2* | 8/2010 | Macfarlane et al. | 600/407 |
| 7,871,406 B2* | 1/2011 | Nields et al. | 606/27 |
| 8,027,712 B2* | 9/2011 | Sioshansi et al. | 600/414 |
| 8,155,416 B2* | 4/2012 | Nields et al. | 382/131 |
| 8,181,995 B2* | 5/2012 | DeCarlo | 285/124.2 |
| 8,224,424 B2 | 7/2012 | Burbank et al. | |
| 8,280,486 B2* | 10/2012 | Miller et al. | 600/414 |
| 8,287,463 B2* | 10/2012 | Field et al. | 600/562 |
| 8,306,602 B2* | 11/2012 | Sirimanne et al. | 600/414 |
| 8,480,665 B2 | 7/2013 | DeCarlo | |
| 8,494,246 B2* | 7/2013 | Trumer et al. | 382/131 |
| 2002/0026187 A1 | 2/2002 | Swanson | |
| 2003/0028095 A1* | 2/2003 | Tulley et al. | 600/422 |
| 2004/0049254 A1* | 3/2004 | Longo | 607/116 |
| 2005/0245920 A1* | 11/2005 | Vitullo et al. | 606/33 |
| 2006/0004351 A1* | 1/2006 | Arless et al. | 606/21 |
| 2006/0173280 A1* | 8/2006 | Goosen et al. | 600/414 |
| 2008/0033286 A1* | 2/2008 | Whitmore et al. | 600/426 |
| 2008/0033424 A1 | 2/2008 | van der Weide et al. | |
| 2008/0269601 A1* | 10/2008 | Schwamb | 600/426 |
| 2009/0018403 A1* | 1/2009 | Black et al. | 600/300 |
| 2009/0080604 A1* | 3/2009 | Shores et al. | 378/37 |
| 2009/0216115 A1* | 8/2009 | Seiler et al. | 600/426 |
| 2010/0234726 A1* | 9/2010 | Sirimanne et al. | 600/426 |
| 2011/0077638 A1* | 3/2011 | Brannan | 606/33 |
| 2011/0118723 A1* | 5/2011 | Turner et al. | 606/33 |
| 2012/0172860 A1* | 7/2012 | Brannan | 606/33 |
| 2012/0259326 A1* | 10/2012 | Brannan et al. | 606/33 |
| 2013/0225942 A1* | 8/2013 | Holsing et al. | 600/301 |
| 2013/0225943 A1 | 8/2013 | Holsing et al. | |
| 2013/0225973 A1* | 8/2013 | Gertner | 600/411 |
| 2013/0225994 A1* | 8/2013 | Hsu et al. | 600/439 |
| 2013/0231556 A1 | 9/2013 | Holsing et al. | |

FOREIGN PATENT DOCUMENTS

| | | |
|---|---|---|
| JP | 2012187405 A | 10/2012 |
| WO | 2011063061 A2 | 5/2011 |
| WO | 2012071388 A2 | 5/2012 |
| WO | 2014025551 A1 | 2/2014 |

OTHER PUBLICATIONS

European Search Report, Application No. EP 14 16 0251 dated Jul. 4, 2014.

Euorpean Search Report, Application No. EP 14 16 0251 dated May 26, 2014.

European Search Report, Application No. EP 14 16 0222 dated May 28, 2014.

European Search Report, Application No. EP 14 16 0223 dated Jun. 3, 2014.

Japanese Office Action, Application No. 2014-104075 dated May 19, 2015.

* cited by examiner

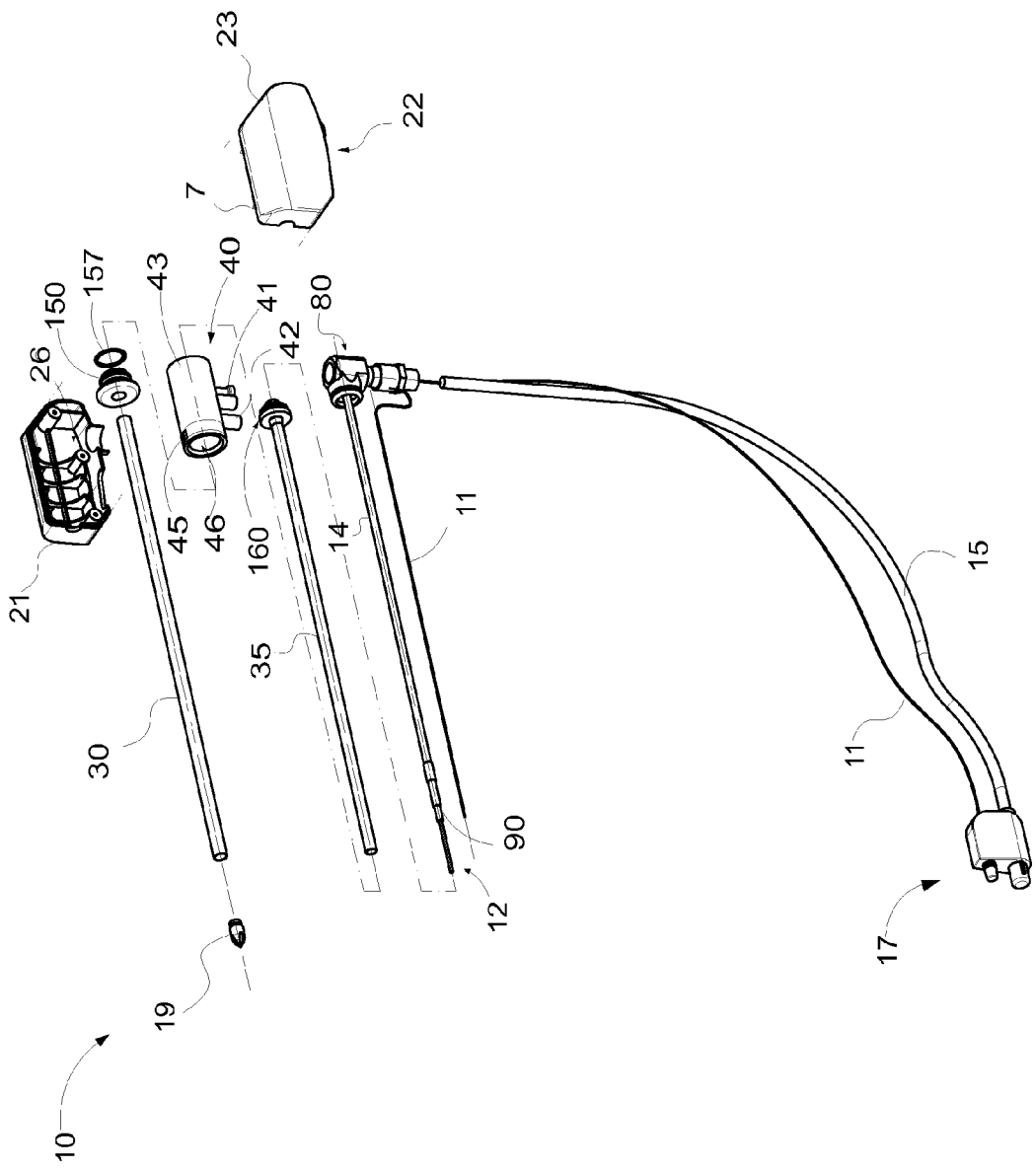

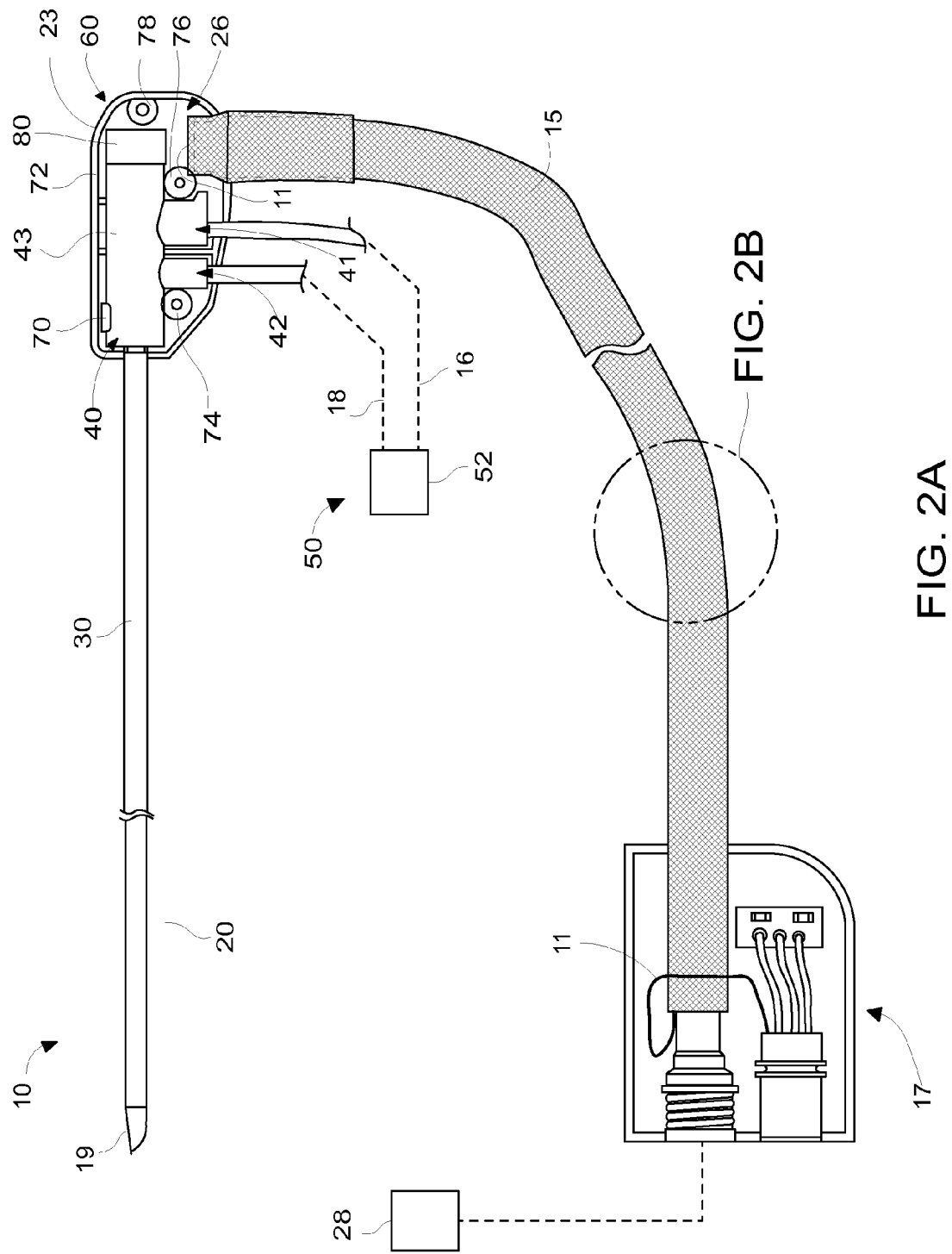

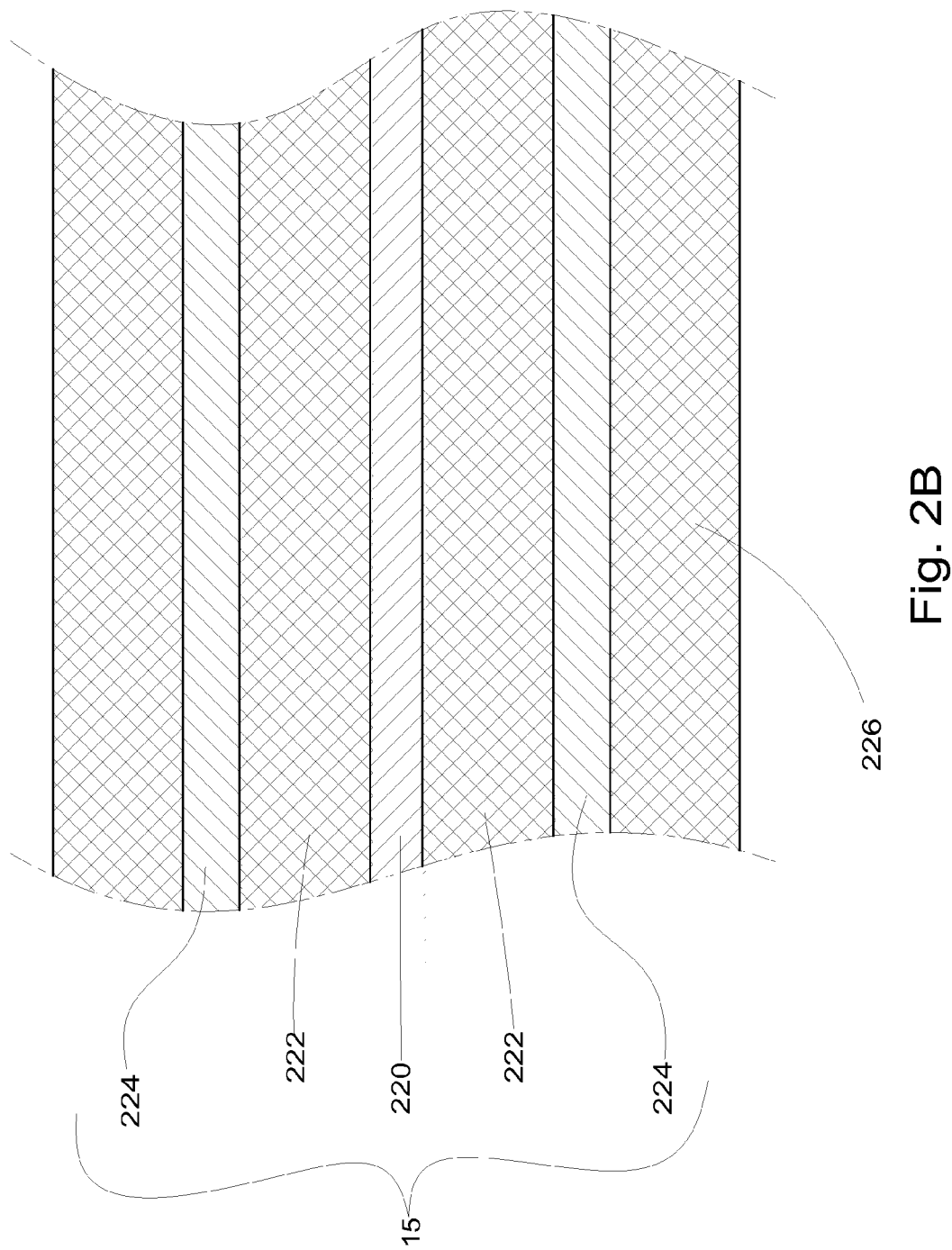

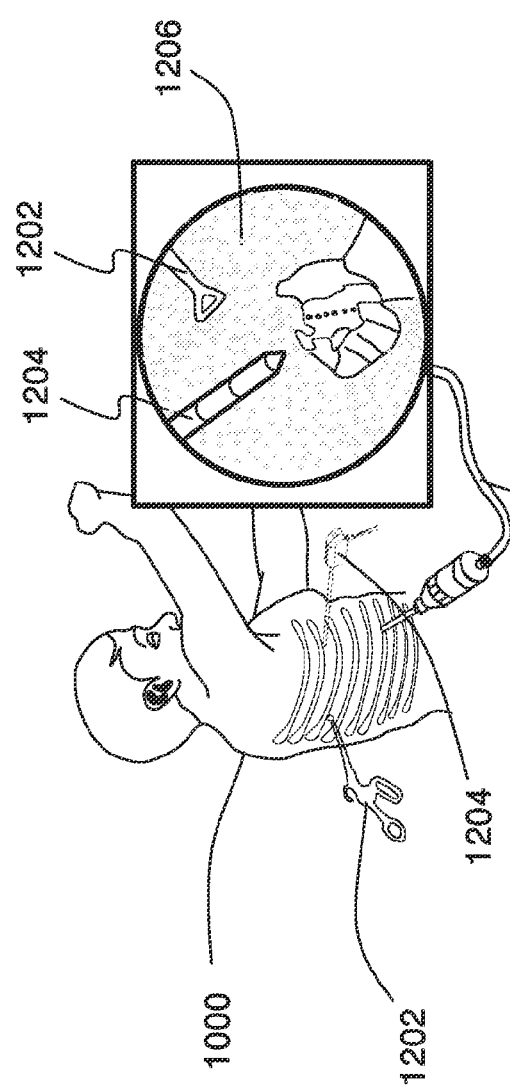
FIG. 16A
FIG. 16B
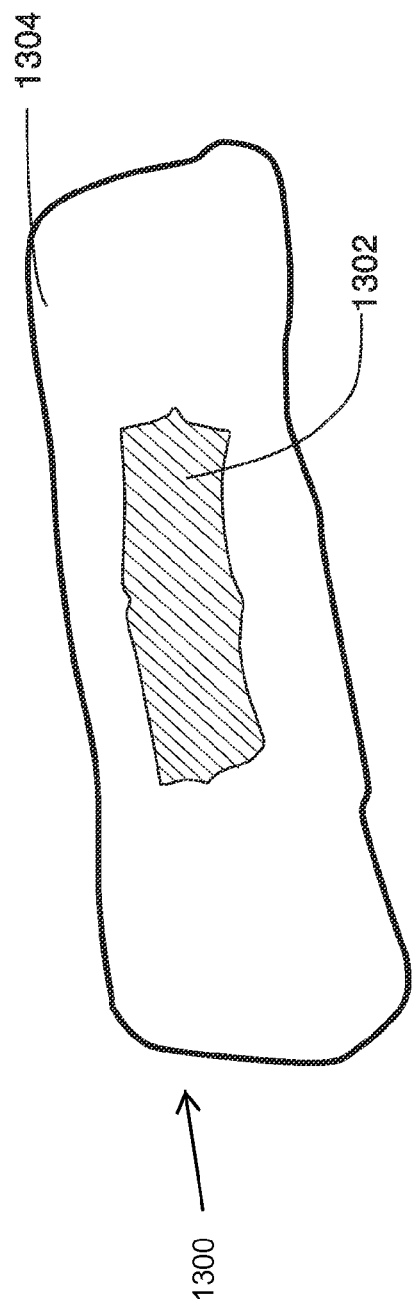
FIG. 17

MICROWAVE ENERGY-DELIVERY DEVICE AND SYSTEM

BACKGROUND

1. Technical Field

The present disclosure relates to microwave surgical devices suitable for use in tissue ablation applications.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat or ablate tissue.

Electrosurgical devices utilizing electromagnetic radiation have been developed for a variety of uses and applications. Typically, apparatus for use in ablation procedures include a power generation source, e.g., a microwave or radio frequency (RF) electrosurgical generator that functions as an energy source and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The particular type of tissue ablation procedure may dictate a particular ablation volume in order to achieve a desired surgical outcome. Ablation volume is correlated with antenna design, antenna performance, antenna impedance, ablation time and wattage, and tissue characteristics, e.g., tissue impedance.

Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to otherwise healthy tissue surrounding the tissue to which electrosurgical energy is being applied. Fluid-cooled or dielectrically-buffered microwave devices may be used in ablation procedures. During operation of the microwave ablation device, if the flow of coolant or buffering fluid is interrupted, the microwave ablation device may exhibit rapid failures due to the heat generated from the increased reflected power.

SUMMARY

One aspect of the present disclosure is directed to a method of manufacturing a microwave ablation device. The method includes applying a balun short circumferentially about an outer conductor of a coaxial feedline, and applying a dielectric material circumferentially about the outer conductor of the coaxial feedline and in contact with the balun short to form a balun. The method further includes extending a temperature sensor along the coaxial feedline such that the sensor contacts the balun short, securing the temperature sensor to the coaxial feedline with a first heat shrink material, and securing the dielectric material, balun short, and temperature sensor in contact with each other and to the coaxial feedline using a second heat shrink material.

The method may also include exposing a distal end of the dielectric material such that it is not covered with the second dielectric material, and applying an electrically conducting ink to the surface of the second heat shrink material facing the dielectric material and balun short. Further the method may include removing a portion of the outer conductor of the coaxial feedline distal of the balun to expose a length of an insulator between the outer conductor and an inner conductor of the coaxial feedline and form a feedpoint. The portion of the outer conductor between the balun and the feed point forms a proximal radiating section.

The method may also include removing a distal portion of the insulator between the inner and outer conductors to expose a distal portion of the inner conductor, and inserting the distal portion of the inner conductor into an electrically-conducting element, the electrically-conductive element forming a distal radiating section of the ablation device. Still further, the method may include inserting a proximal end of the coaxial feedline into a transition, the transition connecting the coaxial feedline to a coaxial cable for connection to a microwave generator.

A further aspect of the present disclosure includes inserting the connected feedline into an inner tubular member, such that at least a portion of the distal radiating section extends beyond the distal end of the inner tubular member. A proximal portion of the inner tubular member may be secured in a hub divider formed of an elastomeric material and having formed therein a substantially non elastic metal ring for securing the proximal portion of the inner tubular member within the hub divider. The method may further include inserting the connected feedline and inner tubular member into a hub, wherein the hub divider and the transition form there between a first chamber. Still further the method may include inserting an outer tubular member into a distal opening formed in a hub cap. Another aspect of the method includes inserting the outer tubular member and hub cap over the inner tubular member in a co-luminal arrangement and into the hub forming a second chamber between the hub cap and hub divider, and placing the hub including inner and outer tubular members, feedline, and transition into a handle body. The handle body may include two housing halves, which when brought together to form the handle body secure the hub including the inner tubular member, the outer tubular member, and transition into place using one or more alignment pins.

BRIEF DESCRIPTION OF THE DRAWINGS

Objects and features of the presently disclosed energy-delivery devices with a fluid-cooled probe assembly and systems including the same will become apparent to those of ordinary skill in the art when descriptions of various embodiments thereof are read with reference to the accompanying drawings, of which:

FIG. 1 is an exploded view of a medical device in accordance with an embodiment of the present disclosure;

FIG. 2A is a schematic diagram of a medical device including a probe, a hub assembly, and a generator connector assembly in accordance with an embodiment of the present disclosure;

FIG. 2B is cross-sectional view of the coaxial cable in accordance with an embodiment of the present disclosure;

FIG. 7C is a cross-sectional view of the probe assembly of FIG. 7A depicting temperature sensors.

FIG. 16A is a side view of a patient undergoing a VATS procedure in accordance with an embodiment of the present disclosure;

FIG. 16B is an image as presented on a video monitor during a VATS procedure in accordance with an embodiment of the present disclosure;

FIG. 17 is a perspective view of a marker in accordance with an embodiment of the present disclosure;

DETAILED DESCRIPTION

Figure 3A:
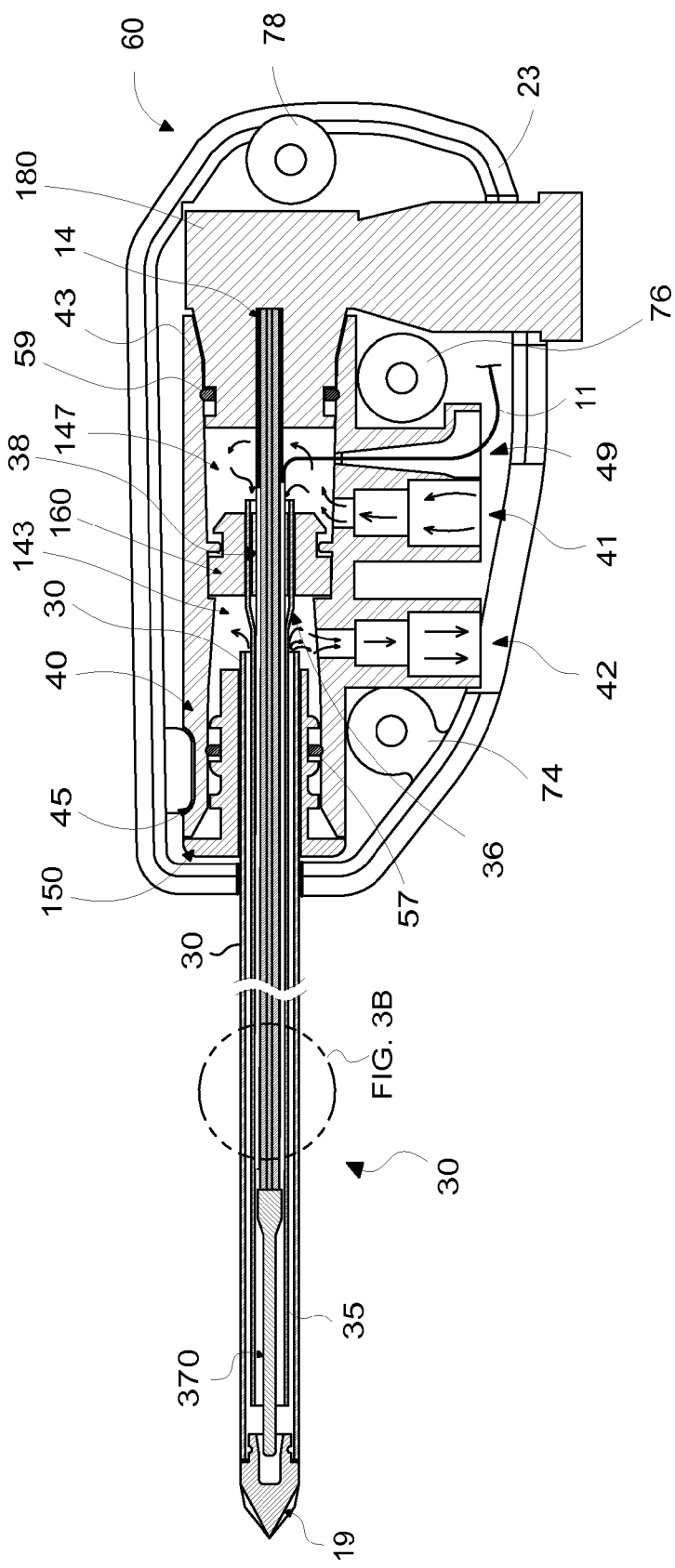
FIG. 3A is an enlarged, cross-sectional view of the probe and hub assembly shown in FIG. 2A in accordance with an embodiment of the present disclosure.

The present disclosure is generally directed to a microwave ablation probe and a system for placement of the probe in a desired location within the body. One aspect of the present disclosure is implementing the percutaneous microwave ablation probe in combination with the i-Logic® target identification, navigation, and marker placement systems developed by superDimension, Ltd. In particular the present disclosure describes devices and systems for the treatment of lung cancer and other lung diseases through microwave ablation of targets identified in the patient for treatment, however the application of the present disclosure and the embodiments described herein are not limited to application of any particular tissue or organ for treatment, indeed, it is contemplated that the systems and methods of the present disclosure may be used to treat liver tissue, kidney tissue, pancreatic tissue, gastrointestinal tissue, interstitial masses, and other portions of the body known to those of skill in the art to be treatable via microwave ablation. These and other aspects of the present disclosure are described in greater detail below.

Hereinafter, embodiments of energy-delivery devices with a fluid-cooled probe assembly and systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as, for example, microwave ablation, radiofrequency (RF) ablation, or microwave or RF ablation-assisted resection.

As it is used in this description, "energy applicator" generally refers to any device that can be used to transfer energy from a power generating source, such as a microwave or RF electrosurgical generator, to tissue. For the purposes herein, the term "energy applicator" is interchangeable with the term "energy-delivery device". As it is used in this description, "transmission line" generally refers to any transmission medium that can be used for the propagation of signals from one point to another. As it is used in this description, "fluid" generally refers to a liquid, a gas or both.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electrical length is in general different from the physical length. By the addition of an appropriate reactive element (capacitive or inductive), the electrical length may be made significantly shorter or longer than the physical length.

Various embodiments of the present disclosure provide an energy-delivery device with a fluid-cooled probe assembly including a balun and temperature sensor disposed in association with the balun. Embodiments may be suitable for utilization in open surgical applications. Embodiments may be suitable for utilization with hand-assisted, endoscopic and laparoscopic surgical procedures such as Video Assisted Thoracic Surgery. Embodiments may be implemented using electromagnetic radiation at microwave frequencies, RF frequencies or at other frequencies. An electrosurgical system including the presently disclosed energy-delivery device with a fluid-cooled probe assembly disposed in fluid communication with a coolant supply system via a hub 40 according to various embodiments is configured to operate at frequencies between about 300 MHz and about 10 GHz. During operation, cooling the probe assembly may enhance the overall heating pattern of the antenna assembly, prevent damage to the antenna assembly, and/or prevent harm to the clinician or patient.

Various embodiments of the presently disclosed energy-delivery device with a fluid-cooled probe assembly including a balun and temperature sensor disposed in association with the balun are suitable for microwave or RF ablation and for use to pre-coagulate tissue for microwave or RF ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of microwave antenna or RF electrode.

FIG. 1 is an exploded view of a medical device 10 in particular the medical device 10 is a microwave antenna. Medical device 10 includes an outer tubular member 30, an inner tubular member 35, a feedline 14, an antenna assembly 12, and a tip 19, which, when assembled, form a probe assembly, or portions thereof. Medical device 10 generally includes two housing halves 21 and 22, which, when assembled, form a handle body 23. Handle body 23 defines a handle-body chamber 26 therein. Medical device 10 includes a hub 40 (as well as other components described herein) disposed, at least in part, within the handle-body chamber 26.

Hub 40 includes a hub body 43 defining a hub-body chamber 46 therein. Medical device 10 includes a hub cap 150 and a hub divider 160, which are configured to be receivable within the hub-body chamber 46 in sealing engagement with the inner walls of the hub body 43. Outer tubular member 30, the inner tubular member 35, the hub 40, and the components cooperative therewith (e.g., hub cap 150 and hub divider 160) are adapted to maintain fluid flow to the antenna assembly 12. Hub body 43 generally includes a first port 41 and a second port 42, e.g., to allow fluid communication with a coolant supply system (e.g., coolant supply system 50 shown in FIG. 2A) via one or more coolant paths (e.g., first coolant path 16 and second coolant path 18 shown in FIG. 2A). First port 41 and the second port 42 may be of any suitable shape, e.g., rectangular, cylindrical, etc., and may include a groove adapted to receive an o-ring or other suitable sealing element.

In some embodiments, the hub body 43 may include one or more mechanical interfaces, e.g., recess 45, adapted to matingly engage with one or more corresponding mechanical interfaces (e.g., tab 70 shown in FIG. 2A) associated with the handle body 23, e.g., to align the hub 40 within the handle body 23 and/or to fixedly secure the hub 40 within the handle-body chamber 26. Similarly, each of the housing halves 21, 22 may include a series of mechanical interfacing components, e.g., alignment pins 74, 76, and 78, configured to matingly engage with a corresponding series of mechanical interfaces (not shown), e.g., to align the two housing halves 21, 22 about the components and assemblies of the medical device 10. It is contemplated that the housing halves (as well as other components described herein) may be assembled together with the aid of alignment pins, snap-like interfaces, tongue and groove interfaces, locking tabs, adhesive ports, etc., utilized either alone or in combination for assembly purposes.

Hub divider 160 is configured and utilized to divide the hub-body chamber 46 into a first chamber, e.g., disposed in fluid communication with the first port 41, and a second chamber, e.g., disposed in fluid communication with the second port 42. The first chamber (e.g., first chamber 147 shown in FIG. 3A) generally fluidly connects the first port 41 to the inner tubular member 35. The second chamber (e.g., second chamber 143 shown in FIG. 3A) generally fluidly connects the second port 42 to the inner tubular member 30.

In some embodiments, the inner walls of the hub body 43 may include a configuration of engagement portions adapted to provide sealing engagement with the hub cap 150 and/or the hub divider 160. In some embodiments, as shown in FIG. 1, an o-ring 157 is provided for engagement with the hub cap 150. O-ring 157 may provide sealing force that permits flexing and/or other slight movement of the hub cap 150 relative to the hub 40 under fluid-pressure conditions. Hub cap 150 and the hub divider 160 are described in more detail later in this disclosure with reference to FIG. 3A.

Figure 3B:
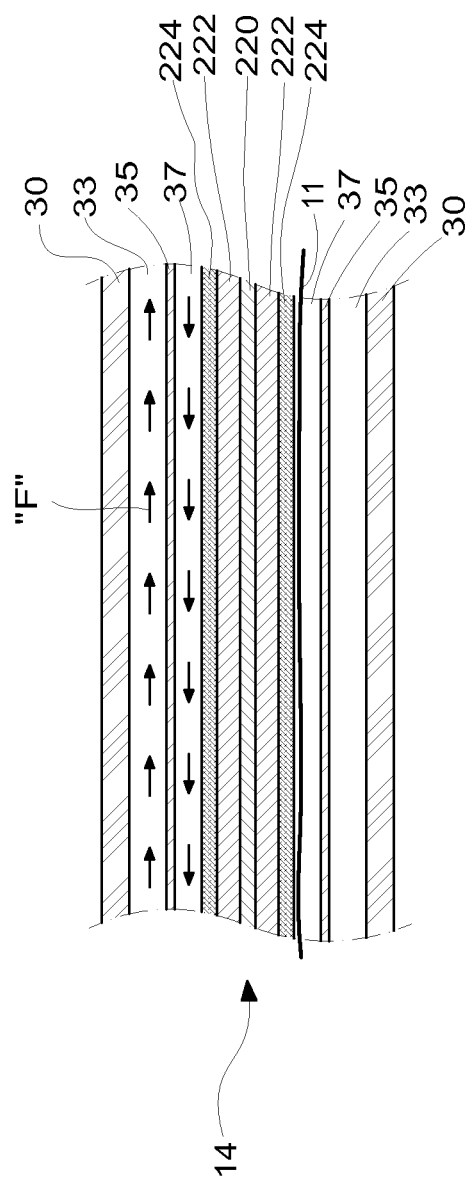
FIG. 3B is an enlarged, cross-sectional view of the indicated area of detail of FIG. 3A, in accordance with an embodiment of the present disclosure.

Outer tubular member 30 and the inner tubular member 35 may be formed of any suitable non-electrically-conductive material, such as, for example, polymeric or ceramic materials. In some embodiments, as shown in FIGS. 3A and 3B, the inner tubular member 35 is coaxially disposed around the feedline 14 and defines a first lumen 37 therebetween, and the outer tubular member 30 is coaxially disposed around the inner tubular member 35 and defines a second lumen 33 therebetween.

Figure 7A:
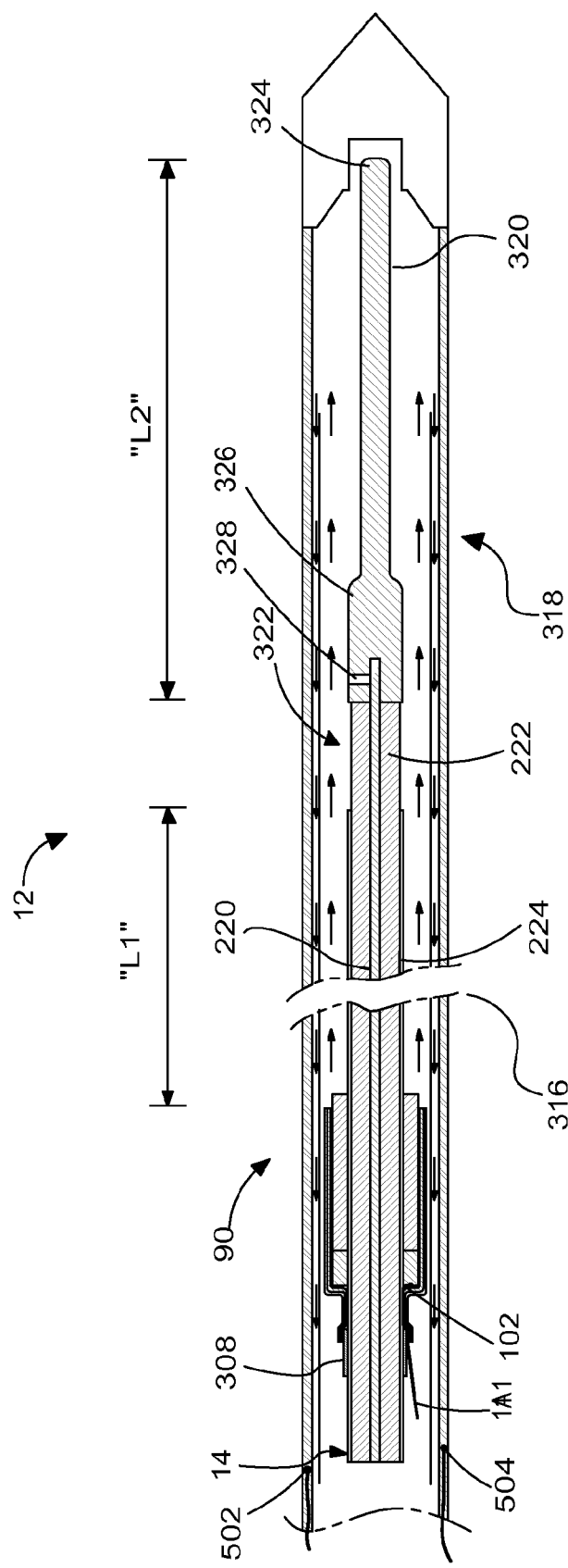
FIG. 7A is a cross-sectional view of a portion of a probe assembly in accordance with an embodiment of the present disclosure.

Probe assembly 20 generally includes an antenna assembly 12 having a first radiating portion (e.g., distal radiating section 318 shown in FIG. 7A) and a second radiating portion (e.g., proximal radiating section 316 shown in FIG. 7A). Antenna assembly 12, which is described in more detail later in this disclosure, is operably coupled by the feedline 14 to a transition assembly 80 shown in FIG. 1, which is adapted to transmit the microwave energy, from the cable assembly 15 to the feedline 14. A connector assembly 17 shown in FIG. 1 is adapted to further operably connect the medical device 10 to a microwave generator 28 (shown in FIG. 2A).

Feedline 14 may be any suitable transmission line, e.g., a coaxial cable. In some embodiments, as shown in FIGS. 3A and 3B, the feedline includes an inner conductor 220, an outer conductor 224 coaxially disposed around the inner conductor 220, and a dielectric material 222 disposed therebetween. Dielectric material 222 may be formed from any suitable dielectric material, e.g., polyethylene, polyethylene terephthalate, polyimide, or polytetrafluoroethylene (PTFE). Inner conductor 220 and the outer conductor 224 may be formed from any suitable electrically-conductive material. In some embodiments, the inner conductor 220 is formed from a first electrically-conductive material (e.g., stainless steel) and the outer conductor 224 is formed from a second electrically-conductive material (e.g., copper). Electrically-conductive materials used to form the feedline 14 may be plated with other materials, e.g., other conductive materials, such as gold or silver, to improve their properties, e.g., to improve conductivity, decrease energy loss, etc. Feedline 14 may have any suitable length defined between its proximal and distal ends. In accordance with various embodiments of the present disclosure, the feedline 14 is coupled at its proximal end to a transition assembly 80 and coupled at its distal end to the antenna assembly 12. Feedline 14 is disposed at least in part within the inner tubular member 35.

FIG. 2A shows a medical device 10 incorporated into an operational system including a microwave generator 28 and a coolant supply system 50. Medical device 10 includes a probe assembly 20 and a handle assembly 60. Probe assembly 20 generally includes the outer tubular member 30, the inner tubular member 35, the feedline 14, the antenna assembly 12, and the tip 19 shown in FIG. 1. Handle assembly 60 generally includes a handle body 23 defining a handle-body chamber 26 therein. Medical device 10 also includes the hub 40 shown in FIG. 1 (as well as other components described herein) disposed, at least in part, within the handle-body chamber 26.

Probe assembly 20 may include a balun 90 (shown in FIGS. 1 and 7) disposed proximal to and spaced apart a suitable length from the feed pint 322. The balun 90, which is described in more detail later in this disclosure, generally includes a balun short, a balun insulator, and an electrically-conductive layer disposed around the outer peripheral surface of the balun insulator, or portions thereof. In some embodiments, the probe assembly 20 includes a temperature sensor 102 (e.g., shown in FIG. 7) disposed in association with the balun 90.

As shown in FIG. 2A, the probe 20 is operably coupled by a cable assembly 15 to a connector assembly 17. Connector assembly 17 is a cable connector suitable to operably connect the medical device 10 to a microwave generator 28. The connector may house a memory (e.g., an EEPROM) storing a variety of information regarding the cable assembly 15 and the medical device 10. For example, the memory may include identification information that can be used by the microwave generator 28 to ensure that only properly identified medical devices 10 are connected thereto. In addition, the memory may store operating parameters of the medical device 10 (e.g., time, power, and dosage limits), cable compensation parameters of the cable assembly 15, and information regarding the usage of the medical device 10 or the cable assembly 15. Usage monitoring may enable limiting re-use of the medical device 10 beyond a certain number of energizations or a single use of the device. Such usage limitations may optionally be reset via reprocessing as is commonly understood in the art. Still further, the connector assembly 17 may include sensor electronics related to radiometry and temperature sensing as described elsewhere herein. Cable assembly 15 may be any suitable, flexible transmission line, and particularly a coaxial cable as shown in FIG. 2B, including an inner conductor 2220, a dielectric material 2222 coaxially surrounding the inner conductor 2220, and an outer conductor 2224 coaxially surrounding the dielectric material 2222. Cable assembly 15 may be provided with an outer coating or sleeve 2226 disposed about the outer conductor 2224. Sleeve 2226 may be formed of any suitable insulative material, and may be may be applied by any suitable method, e.g., heat shrinking, over-molding, coating, spraying, dipping, powder coating, and/or film deposition.

During microwave ablation the probe 20 is inserted into or placed adjacent to tissue and microwave energy is supplied thereto. One or more visualization techniques including Ultrasound, computed tomography (CT), fluoroscopy, and direct visualization may be used to accurately guide the probe 100 into the area of tissue to be treated, as will be described in detail below. Probe 20 may be placed percutaneously or surgically, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 20 may depend on the progress of the heat distribution within the tissue area that is to be destroyed and/or the surrounding tissue.

According to various embodiments, the probe assembly 20 is configured to circulate coolant fluid "F", e.g., saline, water or other suitable coolant fluid, to remove heat generated by the antenna assembly 12 and/or heat that may be generated along the length of the feedline 14, or portions thereof, during the delivery of energy.

In some embodiments, as shown in FIG. 3B, the first lumen 37 is utilized as a fluid inflow conduit and the second lumen 33 is utilized as a fluid outflow conduit. In other embodiments, the first lumen 37 may serve as a fluid outflow conduit and the second lumen 33 may serve as a fluid inflow conduit. Outer tubular member 30 and/or the inner tubular member 35 may be adapted to circulate coolant fluid therethrough, and may include baffles, multiple lumens, flow restricting devices, or other structures that may redirect, concentrate, or disperse flow depending on their shape. The size and shape of the inner tubular member 35, the outer tubular member 30, the first lumen 37, and the second lumen 33 may be varied from the configuration depicted in FIGS. 3A and 3B.

In some embodiments, at least a portion of the inner tubular member 35 and/or at least a portion of the outer tubular member 30 (e.g., a distal portion) may include an integrated, spiraling metallic wire to add shape-memory properties to the probe 20 to aid in placement. In some embodiments, the inner tubular member 35 and/or the outer tubular member 30 may increase in stiffness and exhibit increased shape-memory properties along their length distally toward the antenna assembly 12.

In some embodiments, the first port 41 and the second port 42 are coupled in fluid communication with a coolant supply system 50 via one or more coolant paths 16 and 18 coupled to and in fluid communication with the probe 20 via first and second chambers, 147 and 143 as shown in FIG. 3A. Coolant supply system 50 may be adapted to circulate coolant fluid "F" into and out of the medical device 20. Coolant source 52 may be any suitable housing containing a reservoir of coolant fluid "F", and may maintain coolant fluid "F" at a predetermined temperature. For example, the coolant source 52 may include a cooling unit (not shown) capable of cooling the returning coolant fluid "F" from the antenna assembly 12 via the hub 40.

Coolant fluid "F" may be any suitable fluid that can be used for cooling or buffering the probe assembly 20, e.g., deionized water, or other suitable cooling medium. Coolant fluid "F" may have dielectric properties and may provide dielectric impedance buffering for the antenna assembly 12. Coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

Coolant supply system 50 generally includes a first coolant path 16 leading from the coolant source 52 to the first port 41 (also referred to herein as the fluid inlet port), and a second coolant path 18 leading from the second port 42 (also referred to herein as the fluid outlet port) to the coolant source 52. In some embodiments, the first coolant path 16 includes a coolant supply line 31, e.g., leading from the coolant source 118 to the fluid inlet port 41, and the second coolant path 18 includes a coolant supply line 32, e.g., leading from the coolant source 52 to fluid outlet port 42. In some embodiments, the first coolant path 16 includes a fluid-movement device (not shown) configured to move coolant fluid "F" through the first coolant path 16. Second coolant path 18 may additionally, or alternatively, include a fluid-movement device (not shown) configured to move coolant fluid "F" through the second coolant path 18. Examples of coolant supply system embodiments are disclosed in commonly assigned U.S. patent application Ser. No. 12/566,299 filed on Sep. 24, 2009, entitled "OPTICAL DETECTION OF INTERRUPTED FLUID FLOW TO ABLATION PROBE", and U.S. application Ser. No. 13/835,625 filed on Mar. 15, 2013 entitled "RECIRCULATING COOLING SYSTEM FOR ENERGY DELIVERY DEVICE" the disclosure of which is incorporated herein by reference.

FIG. 3A shows the probe assembly 20 disposed in part within the hub 40, wherein the hub cap 150 and the hub divider 160 are disposed in sealing engagement with the inner walls of the hub body 43, and a proximal portion of the probe assembly 20 is disposed in association with the hub cap 150 and hub divider 160. Hub divider 160 generally divides the hub-body chamber 46 (shown in FIG. 1) into a first chamber 147 a second chamber 143, respectively. First chamber 147 is disposed in fluid communication with the first port 41. Second chamber 143 is disposed in fluid communication with the second port 42. In some embodiments, as shown in FIG. 3A, the proximal end of the inner tubular member 35 is disposed within the first chamber 147, wherein the first lumen 37 is disposed in fluid communication with the first port 41, and the proximal end of the outer tubular member 30 is disposed within the second chamber 143, wherein the second lumen 33 is disposed in fluid communication with the second port 42.

In some embodiments, as shown in FIG. 3A, the inner tubular member 35 includes a first portion having a first outer diameter, a second portion having a second outer diameter greater than the first outer diameter, and a neck portion 36 disposed therebetween. In some embodiments, the opening in the hub divider 160 is configured for sealing engagement with the second portion of inner tubular member 35 having the second outer diameter. In some embodiments, located within the interior of the second portion of the inner tubular member 35 is a high hoop strength metal cylinder 38. The metal cylinder 38 engages the inner diameter of the inner tubular member 35. The hub divider 160 is formed of an elastomeric material and when forced into place within the hub 40, as shown in FIG. 3A, the elastomeric material of the hub divider 160 creates an improved water tight seal separating the first hub chamber 147 from the second hub chamber 143. The metal cylinder 38 improves this seal by ensuring better contact between the elastomeric material of the hub divider 160 and the inner tubular member 35 upon application of lateral forces to the hub divider 160.

Hub body 43 may be configured to sealingly engage the coolant supply lines forming coolant paths 16 and 18 to fluid inlet port 41 and fluid outlet port 42. Fluid inlet port 41 and the fluid outlet port 42 may have any suitable configuration, including without limitation nipple-type inlet fittings, compression fittings, and recesses, and may include an o-ring type elastomeric seal.

FIG. 3B shows a portion of the probe assembly 20 of FIG. 3A including the first lumen 37, shown disposed between the outer tubular member 30 and inner tubular member 35, the second lumen 33, shown disposed between the inner tubular member 35 and the feedline 14, and a transmission line 11 extending longitudinally within the second lumen 33. As indicated by the direction of the arrow-headed lines in FIG. 3B, the first lumen 37 serves as an inflow conduit for coolant fluid "F" and the second lumen 33 serves as an outflow conduit for coolant fluid "F," however as noted above these could be reversed without departing from the scope of the present disclosure.

As shown in FIG. 1, Probe assembly 20 may include a balun 90 disposed proximal to and spaced apart a suitable length from the feed point 322. In some embodiments, the balun 90 may be a quarter-wavelength, ¼ λ, balun, or a ¾ λ balun. Odd harmonics (e.g., ¼ λ, ¼ λ, etc.) may cause a current null at the balun entrance, which helps maintain a desired radiation pattern.

Figure 4:
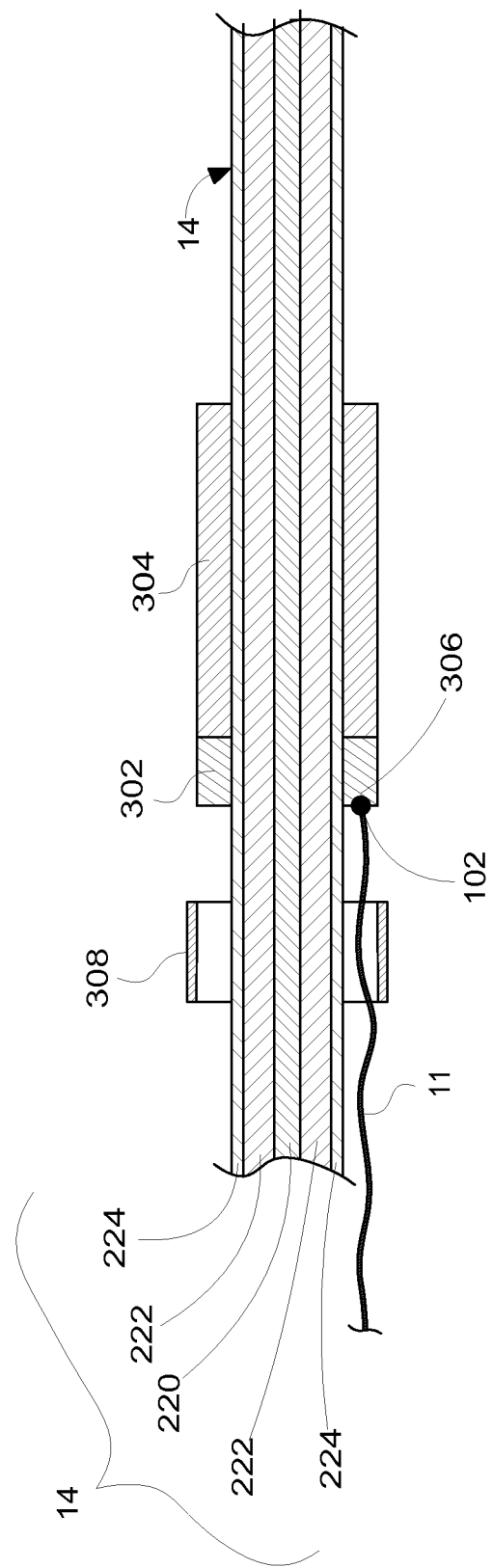
FIG. 4 is an enlarged, cross-sectional view of the portion of the feedline of a probe assembly of the present disclosure during the assembly process in accordance with an embodiment of the present disclosure.
Figure 5:
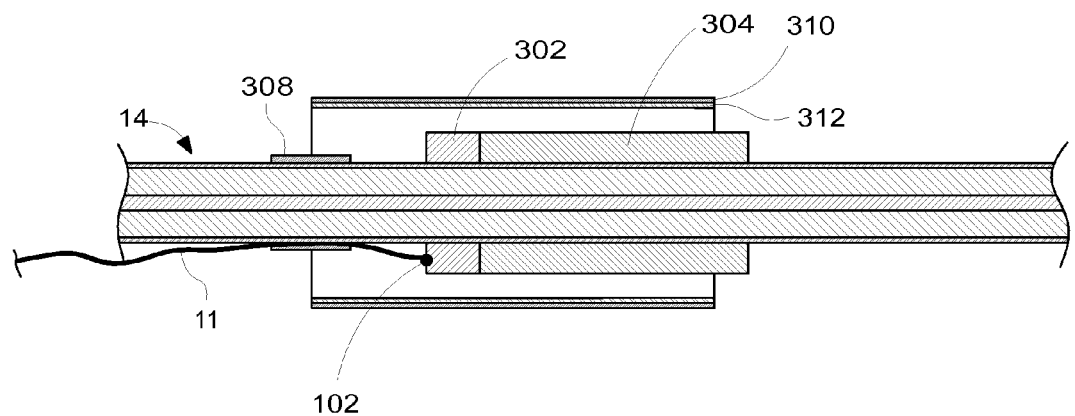
FIG. 5 is an enlarged, cross-sectional view of the portion of the feedline of a probe assembly of the present disclosure during the assembly process in accordance with an embodiment of the present disclosure.
Figure 6:
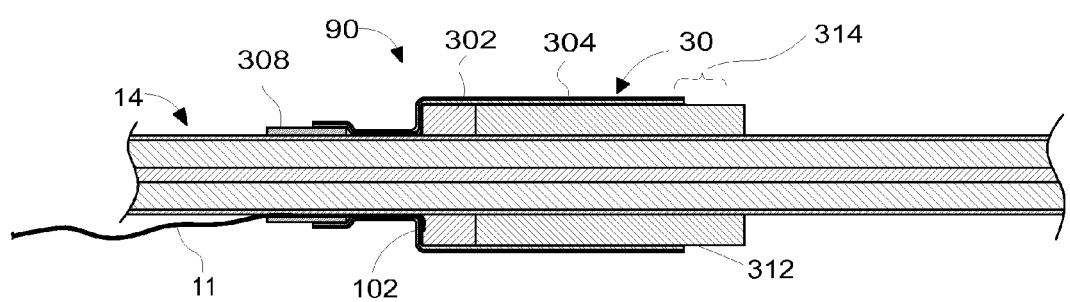
FIG. 6 is an enlarged, cross-sectional view of the portion of a completed feedline in accordance with an embodiment of the present disclosure.

During a manufacturing sequence in accordance with the present disclosure, the component parts of the balun 90, according to the embodiment shown in FIG. 6, are assembled, and, during the manufacturing sequence, as illustratively depicted in FIGS. 4-6, a temperature sensor 102 is coupled to the balun short 302 of the balun 90.

FIG. 4 shows a portion of the feedline 14 including the inner conductor 220, the outer conductor 224 coaxially disposed around the inner conductor 220, and the dielectric material 222 disposed therebetween, shown with a balun short 302 coaxially disposed around a portion of the outer conductor 224. During medical device assembly, balun short 302 is coupled, deposited or otherwise formed onto, or joined to, the outer conductor 224. Balun short 302 may be formed as a single structure and electrically coupled to the outer conductor 224, e.g., by solder or other suitable electrical connection. Balun short 302 may be formed of any suitable electrically-conductive materials, e.g., copper, gold, silver or other conductive metals or metal alloys. In some embodiments, the balun short 302 has a generally ring-like or truncated tubular shape. Balun short 302 is electrically coupled to the outer conductor 224 of the feedline 14 by any suitable manner of electrical connection, e.g., soldering, welding, or laser welding. The size and shape of the balun short 302 may be varied from the configuration depicted in FIG. 4.

FIG. 4 further depicts a dielectric layer 304 (also referred to herein as a balun insulator) coaxially disposed around the outer conductor 224 and coupled thereto. Balun insulator 304 may be formed of any suitable insulative material, including, but not limited to, ceramics, water, mica, polyethylene, polyethylene terephthalate, polyimide, polytetrafluoroethylene (PTFE) (e.g., Teflon®, manufactured by E. I. du Pont de Nemours and Company of Wilmington, Del., United States), glass, metal oxides or other suitable insulator, and may be formed in any suitable manner. In some embodiments, as shown in FIG. 4, the balun insulator 304 is a dielectric sleeve. Balun insulator 304 may be grown, deposited or formed by any other suitable technique. In some embodiments, the balun insulator 304 is formed from a material with a dielectric constant in the range of about 1.7 to about 10.

FIG. 4 further depicts a temperature sensor 102 disposed in contact with a proximal end of the balun short 302. Temperature sensor 102 is coupled to a transmission line 11 extending generally along a longitudinal axis of the feedline 14. In some embodiments, the temperature sensor 102 is a thermocouple and the transmission line 11 is a thermocouple wire. The thermocouple wire may be a two lead wire thermocouple wire, for example it may be comprised of an insulated (anodized) side-by-side constantine wire and a copper wire. The balun short 302 may include an engagement element 306 adapted to engage with the temperature sensor 102, e.g., to facilitate electrical and mechanical coupling of the temperature sensor 102 and the balun short 302. In some embodiments, the engagement element 306 may be a groove, slot, or recess cut into the balun short 302. Alternatively, the temperature sensor 102 may be soldered to balun short 302. Placement of the thermocouple 102 directly against the balun short 302 improves the sensitivity and thermo-profiling characteristics of the medical device 10, particularly as compared to traditional thermocouples in microwave ablation devices, which measure the temperature of the cooling fluid. As will be appreciated by those of skill in the art the temperature of the coolant will lag the temperature of the balun itself, and thus provide only approximate indications of the temperature of the elements which are heated during operation. As a result, in instances where little or no coolant is flowing, the temperature of the balun 90 and feedline 14 associated therewith can increase faster than that of the coolant and result in damage to medical device 10 even before triggering a shut-off of the system based on the temperature the coolant. Accordingly, improved safety and performance can be achieved by direct sensing of temperature of the balun 90.

Still further, FIG. 4 depicts a heat-shrink tubing 308 disposed in a first configuration around the outer conductor. During assembly, the heat-shrink tubing 308 is utilized to secure a portion of the transmission line 11 to the feedline 14. Heat-shrink tubing 308 may be any suitable tubing material with the capability to respond to heat and bind around an object, and may have any suitable length. In some embodiments, the heat-shrink tubing 308 may be a thermoplastic.

FIG. 5 shows the feedline of FIG. 4 following application of heat to the heat shrink tubing 308. During assembly, securing a portion of the transmission line 11 to the feedline 14, as shown in FIG. 6 keeps the transmission line stable and helps to maintain the electrical and mechanical coupling of the temperature sensor 102 and the balun short 302 during subsequent assembly operations. FIG. 5 further shows a second heat shrink tubing 310 disposed in a first configuration.

The tubing member 310 includes an inner layer of an electrically-conductive material 312. Electrically-conductive layer 312 may be formed of any suitable electrically-conductive material, e.g., metallic material. In one embodiment the metallic material of electrically conductive layer 312 is formed of a silver ink deposited or layered on an interior surface of the heat shrink tubing 310. The heat shrink tubing member 310 may have a length from about 1 to about 3 inches in length. However, the shape and size of the tubing member 310 and balun insulator 304 may be varied from the configuration depicted in FIG. 5 without departing from the scope of the present disclosure. Indeed, though described as one embodiment, the orientation and implementation of the feed line 14 as well as other aspects of the present disclosure is not so limited. For example, the feed line 14 may incorporate one or more aspects of the ablation system described in U.S. application Ser. No. 13/836,203 filed on Mar. 15, 2013 entitled "MICROWAVE ABLATION CATHETER AND METHOD OF UTILIZING THE SAME," the entire content of which is incorporated herein by reference.

FIG. 6 shows the balun 90 after the application of thermal energy to the heat shrink tubing 310 and the resultant shrinkage. As shown FIG. 16, the electrically-conductive material 312 is disposed in intimate contact with the balun short 302 and a portion of the balun insulator 304. In some embodiments, as shown in FIG. 6, a portion of the balun insulator 304 may extend distally beyond the distal end of the heat shrink tubing 310 and electrically conductive layer 312, to create gap 314. Gap 314 improves the microwave performance of the probe 20 and can assist in achieving a desired ablation pattern. More specifically, the gap 314 ensures adequate coupling of microwave energy from the proximal radiating section 316 into the balun 90, improving the performance of the balun 90 over a wide range of tissue dielectric conditions. Further, FIG. 6 shows the heat shrink tubing 310 securing the portion of the transmission line 11 between heat shrink tubing 308 and the balun short 302 to the feedline 14 preventing its movement and substantially preventing the temperature sensor 102 from being removed from physical contact with the balun short 302.

FIG. 7A shows a portion of the probe assembly 100 that includes the balun 90 of FIG. 6 connected to the antenna assembly 12. In operation, microwave energy having a wavelength, lambda ($\lambda$), is transmitted through the antenna assembly 12 and radiated into the surrounding medium, e.g., tissue. The length of the antenna for efficient radiation may be dependent on the effective wavelength, $\lambda_{eff}$, which is dependent upon the dielectric properties of the treated medium. Antenna assembly 12 through which microwave energy is transmitted at a wavelength, $\lambda$, may have differing effective wavelengths, $\lambda_{eff}$, depending upon the surrounding medium, e.g., liver tissue as opposed to breast tissue, lung tissue, kidney tissue, etc.

Antenna assembly 12, according to the embodiment shown in FIG. 7, includes a proximal radiating section 316 having a length "L1", a distal radiating section 318 including an electrically-conductive element 320 having a length "L2", and a feed point 322 disposed therebetween. In some embodiments, the proximal radiating section 316 may have a length "L1" in a range from about 0.05 inches to about 0.50 inches. Electrically-conductive element 320 may be formed of any suitable electrically-conductive material, e.g., metal such as stainless steel, aluminum, titanium, copper, or the like. In some embodiments, the electrically-conductive element 320 may have a length "L2" in a range from about 0.15 inches to about 1.0 inches.

As shown in FIG. 7A electrically-conductive element 320 has a stepped configuration, such that the outer diameter of the distal portion 324 is less than the outer diameter of the proximal portion 326. Further, the inner conductor 220 of the feedline 14 is arranged such that it extends past the distal end of the insulator 222 and into the proximal portion 326 of the electrically-conductive element 320. A hole 328, formed in the proximal portion 326 approximately at 90 degrees to the inner conductor 220 allows for solder, a set screw, or other securing mechanisms to physically secure the electrically conductive element 320 to the inner conductor 220 and therewith the feedline 14 of the medical device 20.

Figure 7B:
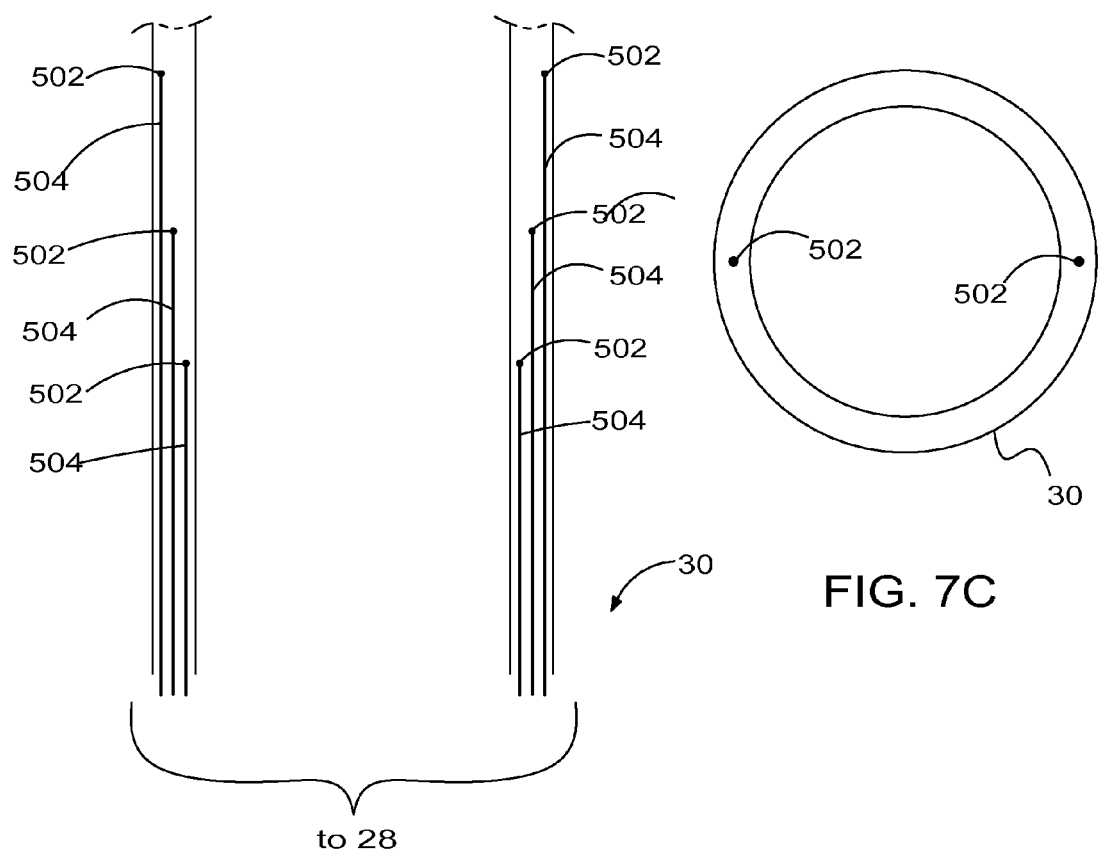
FIG. 7B is a longitudinal cross-sectional view of the probe assembly of FIG. 7A depicting an array of temperature sensors.

FIG. 7B depicts a further embodiment of the present disclosure in which rather than or in addition to the temperature sensor 102 located at the balun short 302, one or more temperature sensors 502 are placed in or on the outer tubular member 30. The outer tubular member 30 formed for example of an epoxy filled glass fiber material. As such the outer tubular member may be formed of a plurality of layers of glass fiber material. During the manufacturing process, one or more temperature sensors 502 may be imbedded in the layup of the glass fiber material. The temperature sensors 502, include wires 504 which connect back to the handle body 23 and ultimately generator 28 or a separate temperature controller (not shown). As an alternative to placing the temperature sensors within the layup of the outer tubular member 30, the outer tubular member 30 may be first formed and then subsequently machined to include one or more slots in which the temperature sensors 502 and wires 504 may be secured, using for example an epoxy material.

According to one embodiment at least one temperature sensor 502 is located at approximately the proximal end of the balun 90. This is approximately the same location as the temperature sensor 102 of FIG. 6 (i.e. about three inches from the distal tip of the medical device 10), but on the outer tubular member 30 as opposed to the balun short 302. This location has been identified as particularly useful in sensing two problems that can occur during operation, no fluid in the medical device 10, and no fluid flow through the medical device 10. These can occur where the clinician fails to connect the cooling system to the medical device or where the clinician fails to turn on the cooling fluid pump, or where there is some other cooling system malfunction. In any instance, the result of the lack of fluid or fluid flow along the outer tubular member 30 can result in it heating to 45° C., which can lead to unintended cell death in the surrounding tissue. The temperature sensors 502 can be employed as a safety indicator and cause the generator 28 to shut down and or issue an alarm as temperatures approach a pre-determined threshold, and thus prevent injury to the patient.

While described above as a single temperature sensor 502, multiple temperature sensors may be used as shown in FIG. 7A. Alternatively, an array of the temperature sensors 502 located at different positions along the length of the outer tubular member 30 may be employed to determine the temperature at different positions along its length as shown in FIG. 7B. These may be at approximately 0.8, 1.0. 1.2, and 1.4 inches from the distal tip of the medical device 10. Using this array, a thermographic profile of the tissue can be created for review and analysis during and after the procedure. For example by sensing the temperature at each temperature sensor 502 the progression of the treatment may be monitored or a terminal threshold of the treatment may be monitored for and end the treatment. The temperature sensors 502 of the array can detect the rising temperature of the ablation field and can be correlated with the ablation growth in the surrounding tissue.

The array of temperature sensors 502 as shown in FIG. 7B may be in addition to the temperature sensor 502 on the outer tubular member at approximately the balun short 302, and/or the temperature sensor 102 in contact with the balun short 302.

In a further embodiment, and as depicted in FIG. 7C, the temperature sensors are located as near the outer periphery of the outer tubular member 30 as possible. In such an embodiment the temperature sensor thus provides a closer approximation of the temperature of the tissue immediately surrounding the outer tubular member 30.

The temperature sensors 502 may be incorporated as part of a temperature monitoring system, e.g., microwave thermometry incorporated into the microwave generator 28 to provide feedback to the generator, or alternatively the temperature monitoring system may be housed in a separate box (not shown) providing audible or visual feedback to the clinician during use of the medical device 10. The temperature sensors 502 are utilized to observe/monitor tissue temperatures in or adjacent an ablation zone. The temperature monitoring system can be, for example, a radiometry system, a thermocouple based system, or any other tissue temperature monitoring system known in the art. In either embodiment, the temperature monitoring system may be configured to provide tissue temperature and ablation zone temperature information to the microwave generator 28 (or other suitable control system).

In at least one embodiment, the tissue temperature and/or ablation zone temperature information may be correlated to specific known ablation zone sizes or configurations that have been gathered through empirical testing and stored in one or more data look-up tables and stored in memory of the temperature monitoring system and/or the microwave generator 28. The configurations may also be based on the observed size and type of tissue to be ablated. Still further, the temperature monitoring system may enable a clinician, having ascertained the size of a target to enter the size into the system and have the system calculate a proposed course of treatment including one or more of a power setting, a number of medical device to be employed, and the duration or number of serial energy applications to achieve a desired ablation zone effective for treating the target tissue. The data look-up tables may be accessible by a processor of the temperature sensing system and/or microwave generator 28 and accessed by the processor while the medical device 10 is energized and treating target tissue. In this embodiment, the temperature sensors 502 provide tissue temperature and/or ablation zone temperature to the microprocessor which then compares the tissue temperature and/or ablation zone temperature to the ablation zone sizes stored in the data look-up tables. The microprocessor may then send a command signal to one or more modules of the temperature sensing monitoring system and/or the generator 28 to automatically adjust the microwave energy output to the medical device 10. Alternatively, a manual adjustment protocol may be utilized to control the microwave energy output to the medical device 10. In this embodiment, the microprocessor may be configured to provide one or more indications (e.g., visual, audio and/or tactile indications) to a user when a particular tissue temperature and/or ablation zone temperature is matched to a corresponding ablation zone diameter or configuration. The temperature monitoring system can incorporated into one or more components (e.g., a software graphical interface configured for display on a monitor 1006

Figure 8:
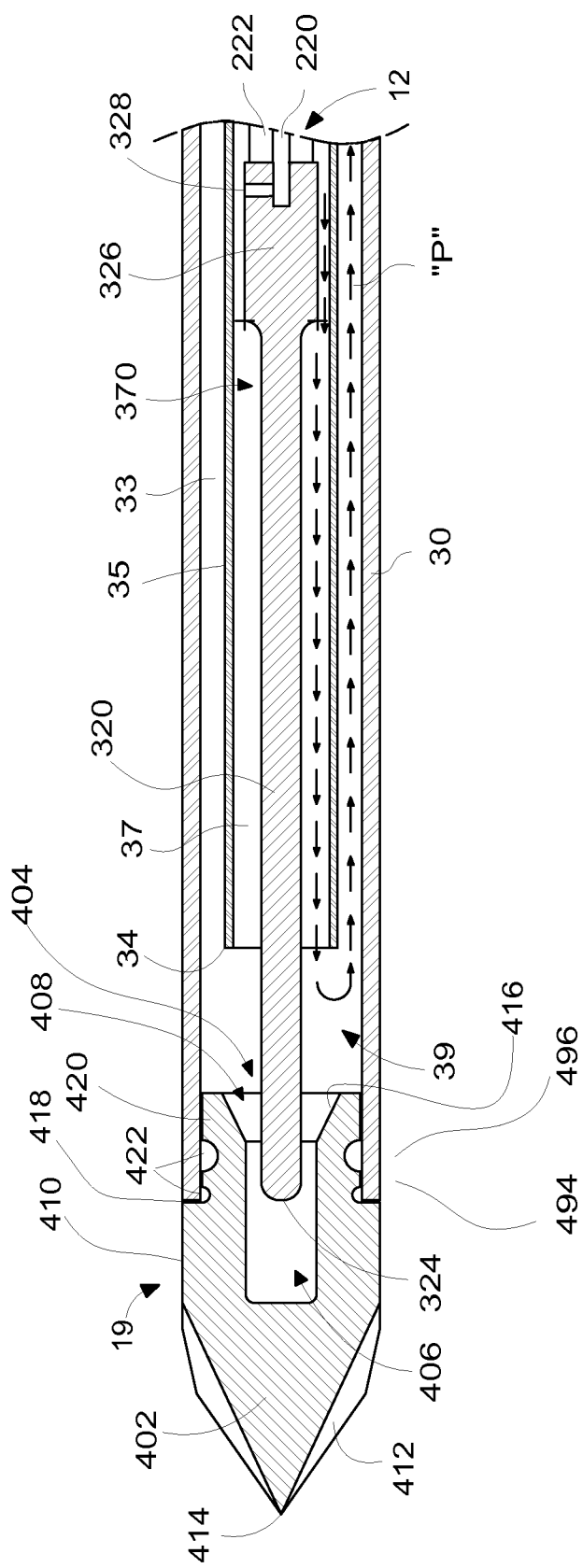
FIG. 8 is an enlarged, cross-sectional view of the distal portions of the probe feedline and radiating portions of a medical device, in accordance with an embodiment of the present disclosure.

FIG. 8 shows a distal portion of the probe assembly 20 including the tip 19, distal portions of the inner and outer tubular members, 35 and 30, respectively, and an inflow/outflow junction 39. Inflow/outflow junction 39 is defined, at least in part, by the outer tubular member 30 and extends distally from the distal end 34 of inner tubular member 35. Tip 19 generally includes a tip body 402 defining an interior chamber 404 disposed within a proximal portion of the tip 19. In some embodiments, the interior chamber 404 includes a distal chamber portion 406 and a proximal chamber portion 408 adapted to be coupled in fluid communication with the inflow/outflow junction 39. Tip body 402 includes a lateral portion 410, and may include a tapered portion 412, which may terminate in a sharp tip 414 to allow for insertion into tissue with minimal resistance. Tapered portion 412 may include other shapes, such as, for example, a tip 414 that is rounded, flat, square, hexagonal, or cylindroconical. In some embodiments, the outer diameter of the lateral portion 410 of the tip body 402 is substantially the same as the outer diameter of the outer tubular member 30.

Tip 19 may be formed of a material having a high dielectric constant, and may be a trocar, e.g., a zirconia ceramic. In some embodiments, the interior chamber 404 is configured to receive a distal end 324 of the electrically-conductive element 320 of the antenna assembly 12. The placement of the distal end 324 within interior chamber 404 in combination the shape of the tip 19 dielectrically buffers electromagnetic energy within close proximity to the antenna assembly 12, specifically around the distal end 324 of the electrically conductive element 320. This arrangement promotes a desirable electromagnetic wave pattern whereby tissue beyond the tip 19 is heated sufficiently to kill diseased cells residing distally away from the probe placement. The projection of electromagnetic energy distally from the tip 19 from the antenna assembly 12 may be described as a microwave field lensing effect. In some embodiments, as shown in FIG. 8, the inner wall of the tip body 402 defining the interior chamber 404 includes a tapered portion 416, e.g., to facilitate the placement of the distal end 324 of the electrically-conductive element 320 into the chamber 404, and/or to facilitate fluid flow between the interior chamber 404 and the inflow/outflow junction 39. The shape and size of the distal chamber portion 406 and the proximal chamber portion 408 may be varied from the configuration depicted in FIG. 8A without departing from the scope of the present disclosure.

In some embodiments, as shown in FIG. 8, the tip body 402 includes a generally L-shaped engagement portion 418 defined, at least in part, by a lateral portion 420 of the tip body 402, wherein the engagement portion 418 is adapted to engage an end portion and the inner surface of the outer tubular member 30. In some embodiments, the outer diameter of the lateral portion 420 of the tip body 402 is less than the inner diameter of the outer tubular member 30, e.g., to provide space for a heat-resistant adhesive material (e.g., material 422 shown in FIG. 8), or other suitable material.

FIG. 8 shows the tip 19 disposed in association with the outer tubular member 30, wherein the distal end 324 of the electrically-conductive element 320 of the antenna assembly 12 is disposed within a portion of the interior chamber 404. Tip 19 and the outer tubular member 30 may be sealingly connected together with a heat-resistant adhesive material 422 or other suitable material, e.g., disposed between the inner wall of the outer tubular member 30 and lateral surface 420 of the tip 19. It is to be understood, however, that sealing engagement between the tip 19 and the outer tubular member 30 may be provided by any suitable technique.

The above-described energy-delivery devices with a fluid-cooled probe assembly are capable of directing energy into tissue, and may be suitable for use in a variety of procedures and operations. The above-described energy-delivery device embodiments may be suitable for utilization with hand-assisted, endoscopic and laparoscopic surgical procedures. The above-described energy-delivery device embodiments may also be suitable for utilization in open surgical applications.

One aspect of the present disclosure is the use of the microwave ablation devices described above used for treatment of cancers and other diseases of the lungs. Location and treatment of lung diseases, particularly cancers due to smoking, is quite challenging due to the tortuous paths of the lung passages, the extremely small size of peripheral lung passages, the movement of the lungs during both diagnostics procedures and treatment.

As a practical matter the most effective method of identifying targets involves the use of a computed tomographic (CT) image. By way of introduction, the use of CT as a diagnostic tool has now become routine and CT results are now frequently the primary source of information available to the practitioner regarding the size and location of a lesion. This information is used by the practitioner in planning an operative procedure such as a biopsy, but is only available as "offline" information which must typically be memorized to the best of the practitioner's ability prior to beginning a procedure. As will be discussed below, in addition to inputting target information, integration with the CT data provides improved system functionality, thereby greatly facilitating the planning of a pathway to an identified target as well as providing the ability to navigate through the body to the target location.

One aspect of the present disclosure relates to a system and method for constructing, selecting and presenting pathway(s) to a target location within an anatomical luminal network in a patient. These embodiments of the present disclosure are particularly, but not exclusively, suited for guiding and navigating a probe through the bronchial airways of the lungs. This embodiment of the present disclosure includes a preoperative and an operative component. The preoperative component is conducted prior to navigation and can be categorized as pathway planning. The operative component is conducted during navigation and can be categorized as navigation.

The pathway planning phase includes three general steps, each of which is described in more detail below. The first step involves using a software graphical interface for generating and viewing a three-dimensional model of the bronchial airway tree ("BT"). The second step involves using the software graphical interface for selection of a pathway on the BT, either automatically, semi-automatically, or manually, if desired. The third step involves an automatic segmentation of the pathway(s) into a set of waypoints along the path that can be visualized on a display. It is to be understood that the airways are being used herein as an example of a branched luminal anatomical network. Hence, the term "BT" is being used in a general sense to represent any such luminal network and not to be construed to only refer to a bronchial tree, despite that the initials "BT" may not apply to other networks.

Figure 9:
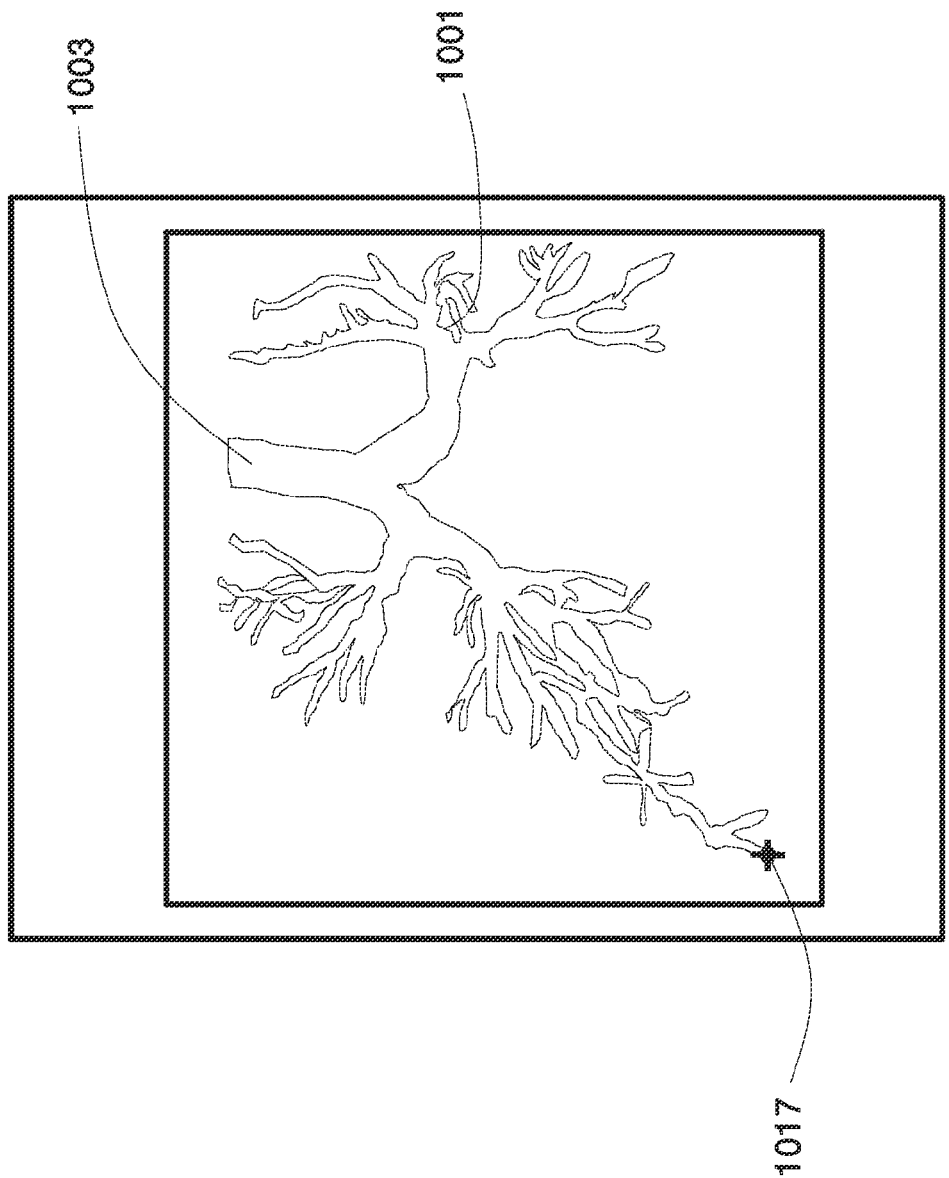
FIG. 9 is a screen shot of a CT based luminal navigation system in accordance with an embodiment of the present disclosure.

Using a software graphical interface 1001 as shown in FIG. 9, for generating and viewing a BT, starts with importing CT scan images of a patient's lungs, preferably in a DICOM format, into the software. The data may be imported into the software using any data transfer media, including but not limited to CDs, memory cards, network connections, etc. The software processes the CT scans and assembles them into a three-dimensional CT volume by arranging the scans in the order they were taken and spacing them apart according to the setting on the CT when they were taken. The software may perform a data fill function to create a seamless three-dimensional model. The software uses the newly-constructed CT volume to generate a three-dimensional map, or BT, of the airways. The three dimensional map can either be skeletonized, such that each airway is represented as a line, or it may be include airways having dimensions representative of their respective diameters. Preferably, when the BT is being generated, the airways are marked with an airflow direction (inhalation, exhalation, or separate arrows for each) for later use during the pathway generation step. The software then displays a representation of the three-dimensional map 1003 on the software graphical interface 1001.

Figure 10:
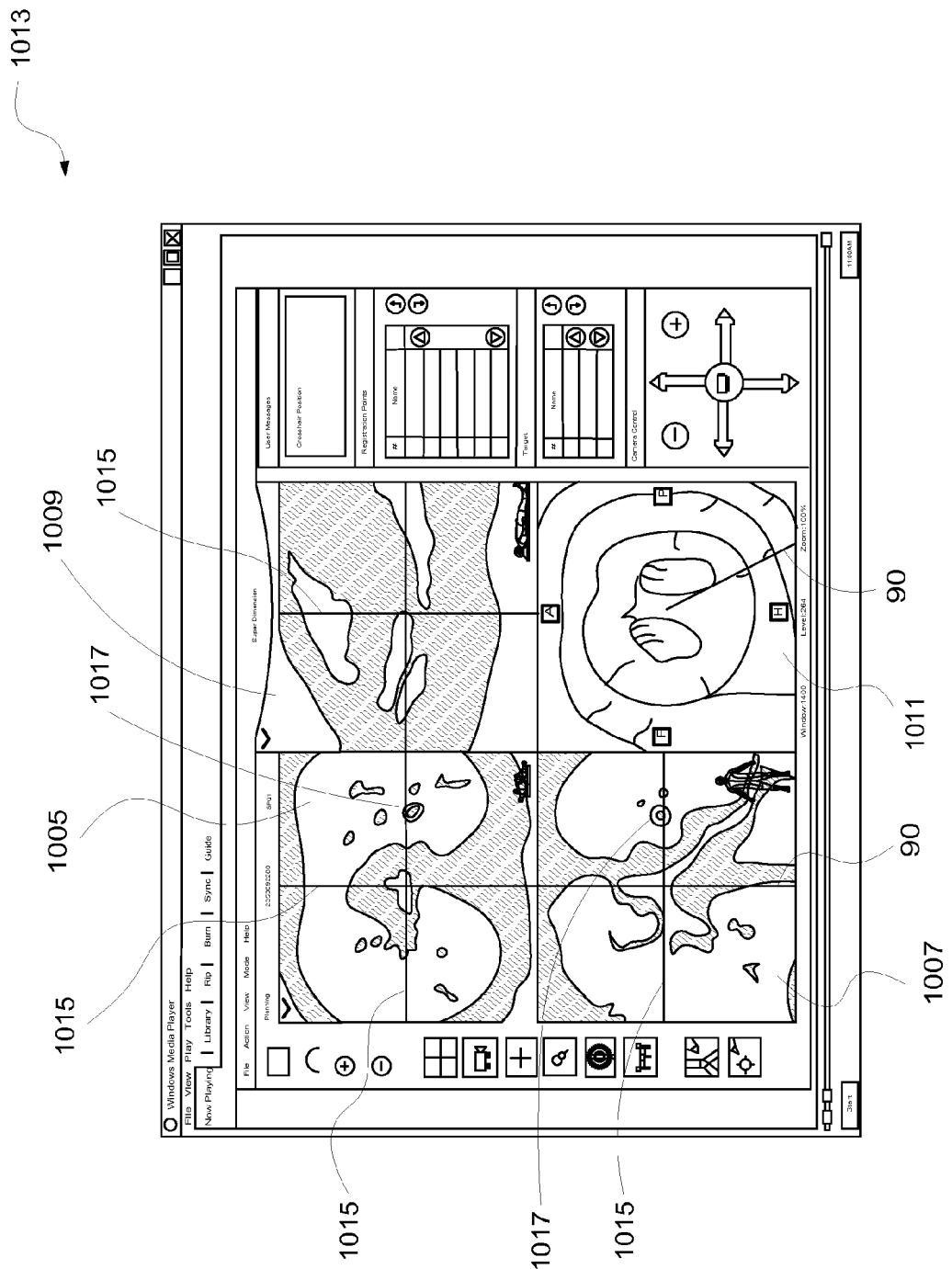
FIG. 10 is a screen shot of a CT based luminal navigation system in accordance with an embodiment of the present disclosure.

FIG. 10 depicts a further software graphical interface 1013 in which three views of the CT image are presented along with a computer generated model of the interior of the BT. As shown, the top left image 1005 is the lateral view of the CT volume of the lungs, i.e. as though looking parallel to the spine of the patient. The lower-left image 1007 is a birds-eye view of the CT volume of the lungs. The upper-right image 1009 is a side view of the CT volume of the lungs. Finally, the lower-right image 1011 is a three-dimensional perspective view inside a virtual airway of the BT. Cross-hairs 1015 span over three of the images to show the position in the CT image in all three planes.

A user presented with the graphical interface 1013 is able to scroll through the CT image, in any of the presented views and identify one or more targets. These targets are typically masses or tumors that the medical professional would like to biopsy or treat, and to which the medical professional would like to use the system to navigate. Once one or more targets are identified in the images 1005-1009, and selected by a medical professional using the target selection tool incorporated in the software, the targets automatically appear on the image of the BT as targets 1017 in FIG. 10.

Next, the software selects a pathway to the target. In one embodiment, the software includes an algorithm that does this by beginning at the selected target and following lumina back to the entry point. Using the airways as an example, the target is first selected. The software then selects a point in the airways nearest the target. If the point closest to the target is in an airway segment that is between branches, the software has to choose between two directional choices. The pathway to the target may be determined using airway diameter. Moving toward the entry point (the trachea) results in an increased airway diameter while moving distally results in a decreased airway diameter. If the point closest to the target is in an airway segment that includes one or more branches, the choices are more numerous but the following the path of the greatest increase in airway diameter will still result in the correct path to the entry point. Though unlikely, in the event that an incorrect path is taken, the software would eventually detect an inevitable decrease in diameter, if this is the case, the software would automatically abort that path and revert to the last decision-making point. The algorithm will resume, blocking off the incorrect path as an option.

After the pathway has been determined, or concurrently with the pathway determination, the suggested pathway is displayed for user review. Preferably, the entire BT will be displayed with the suggested pathway highlighted in some fashion. The user will have zoom and pan functions for customizing the display. This is important as the software may identify a solution that rotation or zooming of the BT will show is less than ideal. For example, a planned route may include a 90 degree turn to reach the target. Such turns are nearly impossible for current catheter systems, as will be described in greater detail below, to accomplish, particularly as the airway passages become smaller. Thus, by rotating and zooming the image, a medical professional can determine a preferable route (e.g., one where the target is accessed in a more direct line from the airway). There may be additional reasons for editing the pathway, for example, though the targeted lesion is closest to a particular airway, there may be an artery or a lobe division between the selected airway and the target. Hence, it is important to provide the user with editing ability. In addition to the above described techniques for determining a pathway to a target, the present disclosure may also employ the techniques described in commonly assigned U.S. application Ser. No. 13/838,805 filed on Mar. 15, 2013 entitled "PATHWAY PLANNING SYSTEM AND METHOD," the entire contents of which is incorporated herein by reference.

This image 1011 is a CT-based "virtual bronchoscopy" which depicts simulated views similar to the actual bronchoscope views. The technology of virtual bronchoscopy is described in commonly assigned U.S. Pat. Nos. 6,246,784 and 6,345,112 both to Summers et al., as well as the references cited therein, all of which are hereby incorporated herein by reference. Once the pathway is edited, as necessary, the user can follow a fly-through virtual bronchoscopy image 1011. The software generates a colored line which represents the pathway determined above. The medical professional is to follow the pathway through the trachea, and the airways until reaching the target. As can be appreciated, as the airways get smaller and smaller the ability of the software to resolve the airways becomes increasingly difficult, and the display 1011 may eventually not depict a clear airway lumen. Regardless, the target 1017 will be displayed in the computer generated image 1011 and allow the utilization of the system for pathway planning purposes.

Figure 11:
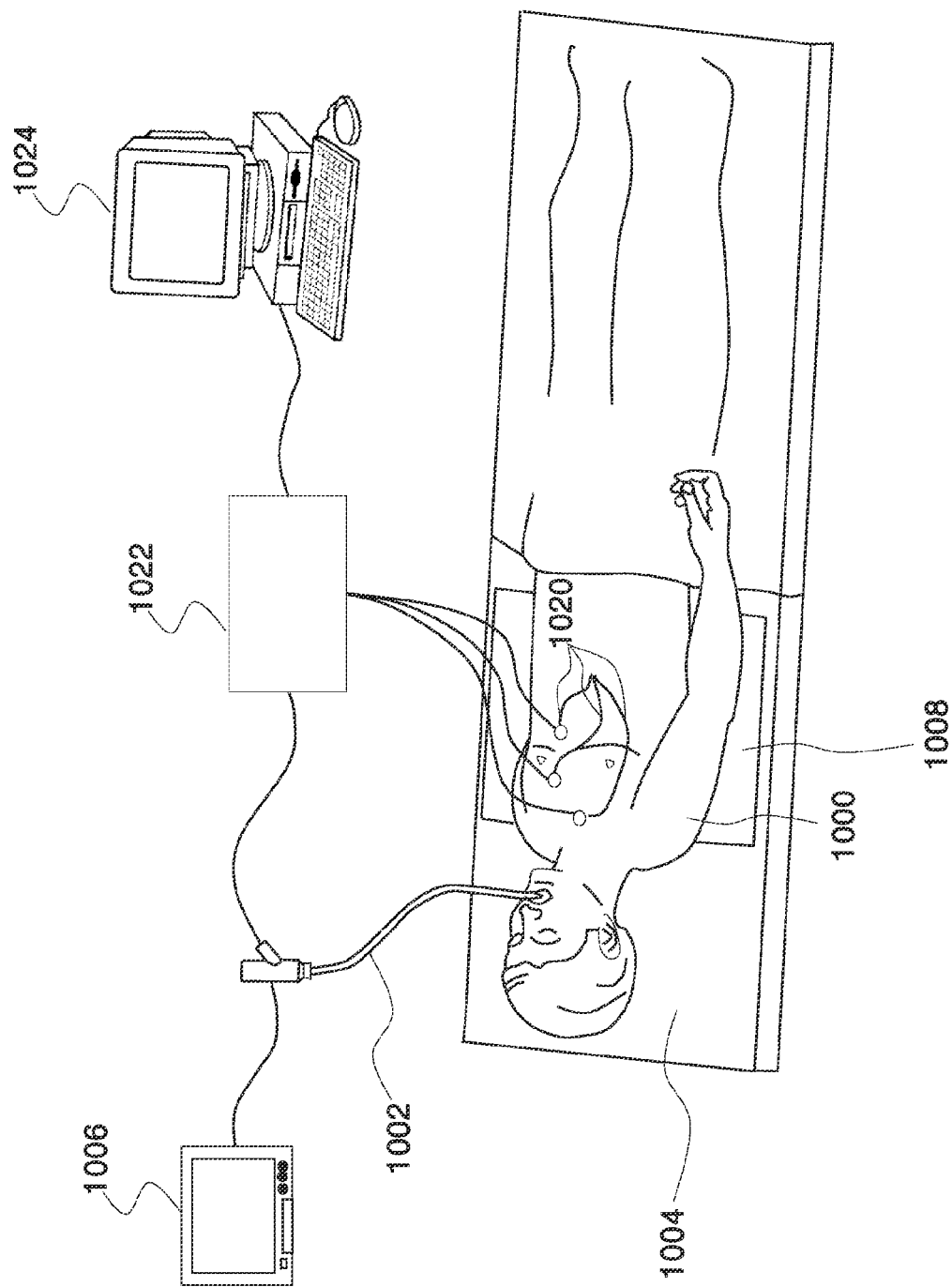
FIG. 11 is perspective view of a luminal navigation system in accordance with an embodiment of the present disclosure.

Having identified a pathway in the BT connecting the trachea in a CT image with a target, a system is necessary to reach the target for biopsy of the target and eventually treatment if necessary. One such system is depicted in FIG. 11. Specifically, FIG. 11 shows a patient 1000 lying on an operating table 1002. A bronchoscope 1004 is inserted into his lungs. Bronchoscope 1004 is connected to the monitoring equipment 1006, and typically includes a source of illumination and a video imaging system. In certain cases, the devices of the present disclosure may be used without a bronchoscope, as will be described below. A position measuring system monitors the position of the patient 1000, thereby defining a set of reference coordinates. A particularly preferred position measuring system is a six degrees-of-freedom electromagnetic position measuring system according to the teachings of U.S. Pat. No. 6,188,355 and published PCT Application Nos. WO 00/10456 and WO 01/67035, which are incorporated herein by reference. In this case, a transmitter arrangement 1008 is implemented as a matt positioned beneath patient 1000. A number of miniature sensors 1020 are interconnected with a tracking module 1022 which derives the location of each sensor 1020 in 6 DOF (degrees of freedom). At least one, and preferably three, reference sensors 1020 are attached to the chest of patient 1000 and their 6 DOF coordinates sent to a computer 1024 where they are used to calculate the patient coordinate frame of reference.

Figure 12:
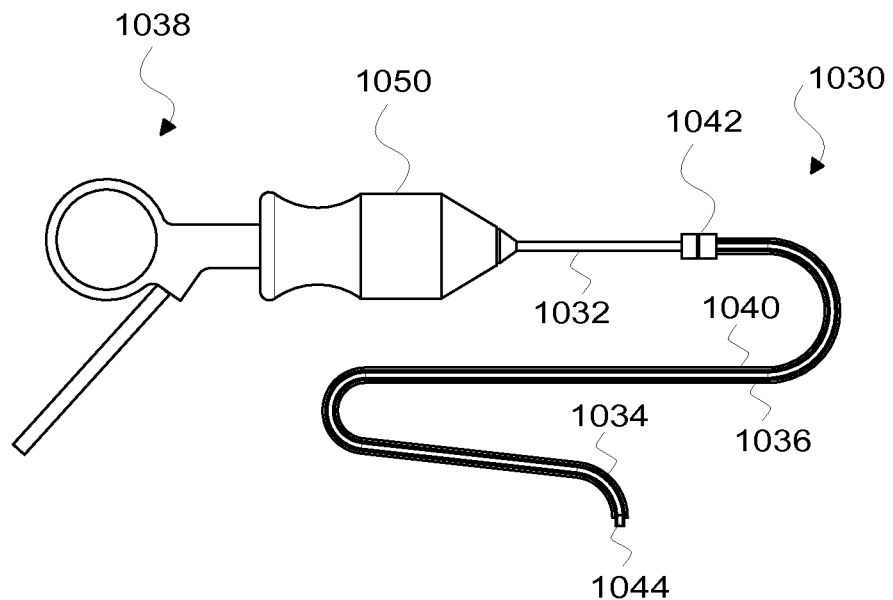
FIG. 12 is a side view of a luminal catheter delivery assembly in accordance with an embodiment of the present disclosure.

FIG. 12 depicts a catheter assembly 1030, constructed and operative according to the teachings of the present disclosure. Catheter assembly 1030 includes a locatable guide 1032 which has a steerable distal tip 1034, a flexible body 1036 and, at its proximal end, a control handle 1038. Guide 1032 is inserted into a sheath 1040 within which it is locked in position by a locking mechanism 1042. A position sensor element 1044, operating as part of the position measuring system of FIG. 11, is integrated with distal tip 1034 and allows monitoring of the tip position and orientation (6 DOF) relative to the reference coordinate system.

Figure 13:
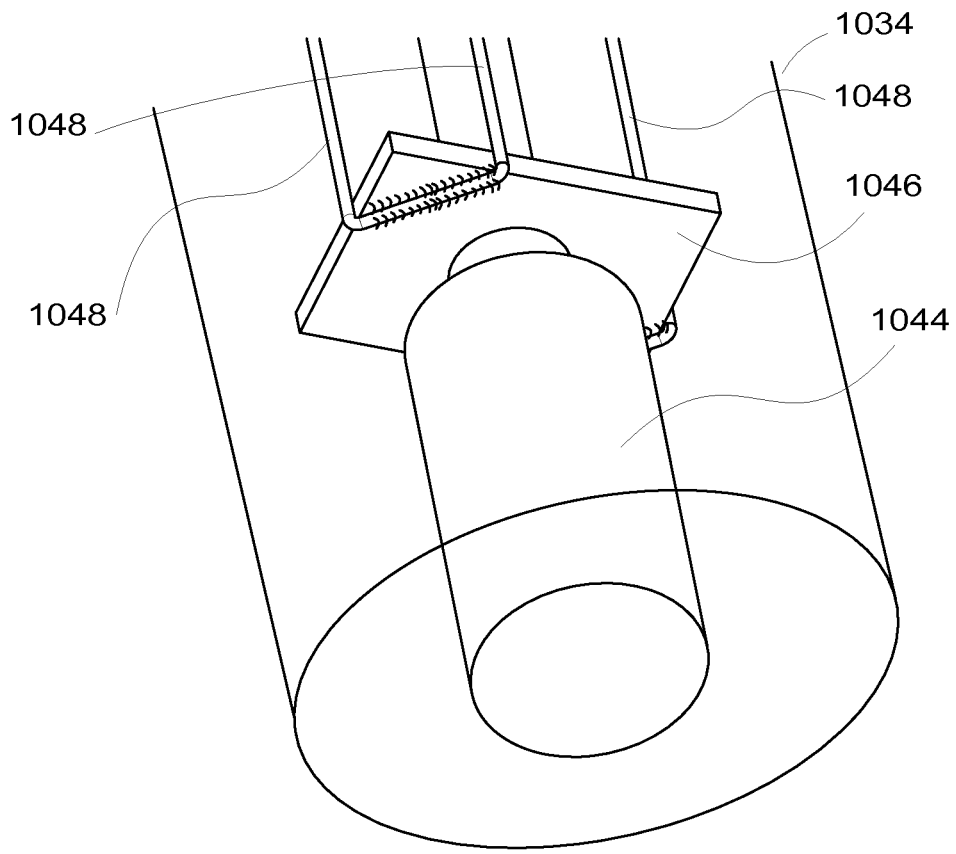
FIG. 13 is a perspective view of a catheter manipulation system in accordance with an embodiment of the present disclosure.

There are several methods of steering the catheter 30. In a first method, a single direction of deflection may be employed. Alternatively, a multi-directional steering mechanism with a manual direction selector may be employed to allow selection of a steering direction by the practitioner without necessitating rotation of the catheter body. FIG. 13 depicts a system for multi-directional steering using at least three, and preferably four, elongated tensioning elements ("steering wires") 1048 are attached. Steering wires 1048 are deployed such that tension on each wire individually will steer the tip towards a predefined lateral direction. In the case of four wires, the directions are chosen to be opposite directions along two perpendicular axes. In other words, the four wires are deployed such that each wire, when actuated alone, causes deflection of said tip in a different one of four predefined directions separated substantially by multiples of 90°. For practical reasons of ease of manufacture and reliability, wires 1048 are preferably implemented as pairs of wires formed from a single long wire extending from handle 1038 to tip 1034, bent over part of base 1046, and returning to handle 1038, as shown.

Figure 14:
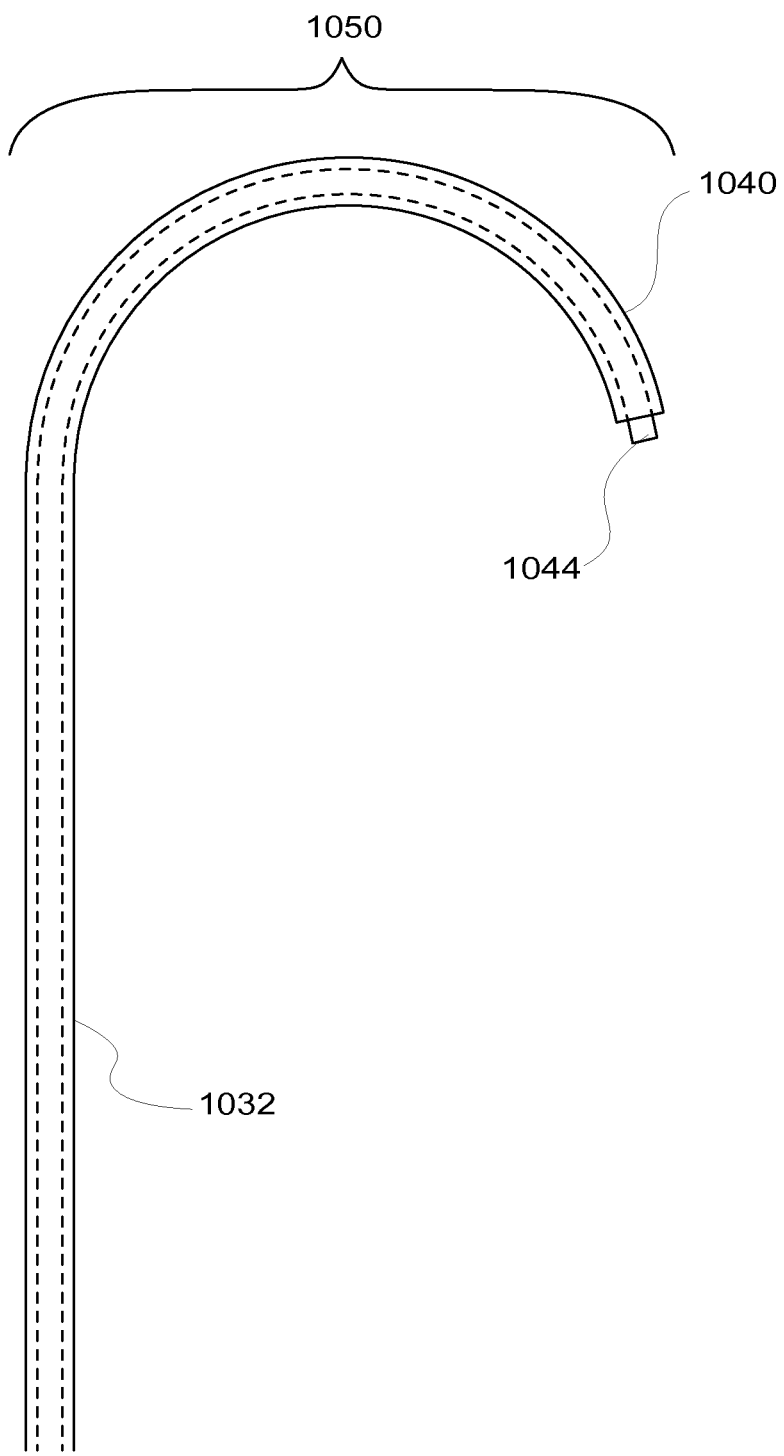
FIG. 14 is a side view of a catheter in accordance with an embodiment of the present disclosure.

A third alternative employs a catheter assembly 1030 having a curved or hooked configuration as shown in FIG. 14. In such a system, it is the catheter sheath 1040 that is formed with a curved tip 1050. The locatable guide 1032 is inserted into the sheath 1040 such that the sensor element 1044 projects from the distal tip of the sheath 1040. The sheath 1040 and the locatable guide 1032 are locked together such that they are advanced together into the lung passages of the patient 1000. The user when needing to select a path for further insertion of the catheter assembly 1030 simply rotates the locked together sheath 1040 and locatable guide 1032. It has been found that the pre-forming of the curved tip 1050 of the sheath 1040 facilitates advancement by requiring only one hand of the user, and minimizing fatiguing motions such as squeezing of the control handle 1038 to release a locking mechanism or to advance the sheath 1040 or locatable guide 1032. This alternative is currently marketed by Covidien LP under the name EDGE®. Differing amounts of pre-curve implemented in the sheath 1040 can be used, however, common curvatures include 45, 90, and 180 degrees. The 180 degree sheath has been found particular useful for directing the locatable guide 1032 to posterior portions of the upper lobe of the lung which can be particularly difficult to navigate.

As noted above, the present disclosure employs CT data (images) for the route planning phase. CT data is also used for the navigation phase. CT data is preferable to other imaging modalities because it has its own system of coordinates. Matching the two systems of coordinates, that of the CT and that of the patient, is commonly known as registration. Registration is generally performed by identifying locations in both the CT and on or inside the body, and measuring their coordinates in both systems.

Methods of manual and semi-automated registration of CT data and patient data are described in detail in for example U.S. Pat. No. 7,233,820 assigned to Covidien LP and incorporated herein by reference. While still a viable methods of registration, because particularly manual registration is somewhat time consuming and requires multiple steps, many practitioners rely on the automatic registration techniques the software of the current disclosure enables. However, in some instances, particularly if the CT image data is not of sufficient quality it may still be necessary or desirable to conduct manual registration.

Automatic registration has become the norm for most procedures because while the manual fiducial point designation of the above referenced registration techniques is highly effective, the choice of number of points sampled necessarily represents a tradeoff between accuracy and efficiency. Similarly, while the semi-automated technique is a viable option it requires an image sensor at the distal end of the catheter assembly which adds increased complexity to the system.

Automatic registration techniques are described in detail in commonly assigned U.S. patent application Ser. No. 12/780, 678, which is incorporated herein by reference. Automatic registration between a digital image of a branched structure and a real-time indicator representing a location of a sensor inside the branched structure is achieved by using the sensor 1044 to "paint" a digital picture of the inside of the structure. Once enough location data has been collected, registration is achieved. The registration is "automatic" in the sense that navigation through the branched structure necessarily results in the collection of additional location data and, as a result, registration is continually refined.

The automatic registration method comprises the following steps and a system is adapted to perform the following steps: moving a locatable guide 1032 containing a location sensor 1044 within a branched structure of a patient 1000; recording data pertaining to locations of said sensor while said sensor is moving through said branched structure using the transmitter arrangement 1008; comparing a shape resulting from said data to an interior geometry of passages of said three-dimensional model of said branched structure; and determining a location correlation between said shape and said three-dimensional model based on said comparison.

Another aspect of the method comprises the following steps performed by the software of the present disclosure: identifying non-tissue space (e.g. air filled cavities) in said three-dimensional model; moving a locatable guide 1032 through at least one lumen of said branched structure while recording position data of a location sensor 1044 in said locatable guide 1032; and aligning an image representing a location of said probe with an image of said three-dimensional model based on said recorded position data and an assumption that said probe remains located in non-tissue space in said branched structure. Thus the software is capable of performing steps of comparing a shape, and determining a location correlation, or aligning an image.

The registration techniques operates on the premises that (1) the endoscope remains in the airways at all times and (2) recording the movement of a sensor on an endoscope results in a vastly greater sample set than recording discrete positions of a sensor on a stationary endoscope.

The registration methods may be referred to as "feature-based registration." When the CT scans are taken, the CT machine records each image as a plurality of pixels. When the various scans are assembled together to form a CT volume, voxels (volumetric pixels) appear and can be defined as volume elements, representing values on a regular grid in three dimensional space. Each of the voxels is assigned a number based on the tissue density Hounsfield number. This density value can be associated with gray level or color using well known window-leveling techniques.

The sensing volume of the electromagnetic field of the transmitter arrangement 1008 is also voxelized by digitizing it into voxels of a specific size compatible with the CT volume. Each voxel visited by the location sensor 1044 can be assigned a value that correlates to the frequency with which that voxel is visited by the location sensor 1044. The densities of the voxels in the CT volume are adjusted according to these values, thereby creating clouds of voxels in the CT volume having varying densities. These voxel clouds or clusters thus match the interior anatomical features of the lungs.

By using a voxel-based approach, registration is actually accomplished by comparing anatomical cavity features to cavity voxels, as opposed to anatomical shapes or locations to structure shapes or locations. An advantage of this approach is that air-filled cavities are of a predictable range of densities. Air filled cavities may be identified as non-tissue space in the CT volume, which is a three-dimensional model. The location sensor 1044 may be moved through the lumen while recording position data thereof. This allows for aligning an image representing a location of said location sensor with an image of said three-dimensional model based on said recorded position data and an assumption that said probe remains located in non-tissue space. When moving the location sensor 1044 within a branched structure, data is recorded pertaining to locations of the location sensor 1044 while it is moving through said branched structure. Then a shape resulting from said data is compared to an interior geometry of passages of said three-dimensional model of said branched structure generated from the CT data. This provides for determining a location correlation between said shape and said three-dimensional model based on said comparison.

Registration using the technique of the present disclosure is accomplished by placing a location sensor 1044 into the airways and continually recording its position. This continues until there is enough data for a shape-matching algorithm to determine that the "painted" shape can only fit within the 3D CT volume in one place and orientation. Another way to accomplish initial registration is to simply navigate the probe down a plurality of various airways, preferably selected in both lungs. As stated above, the more airways visited, the smaller the registration error.

Figure 15:
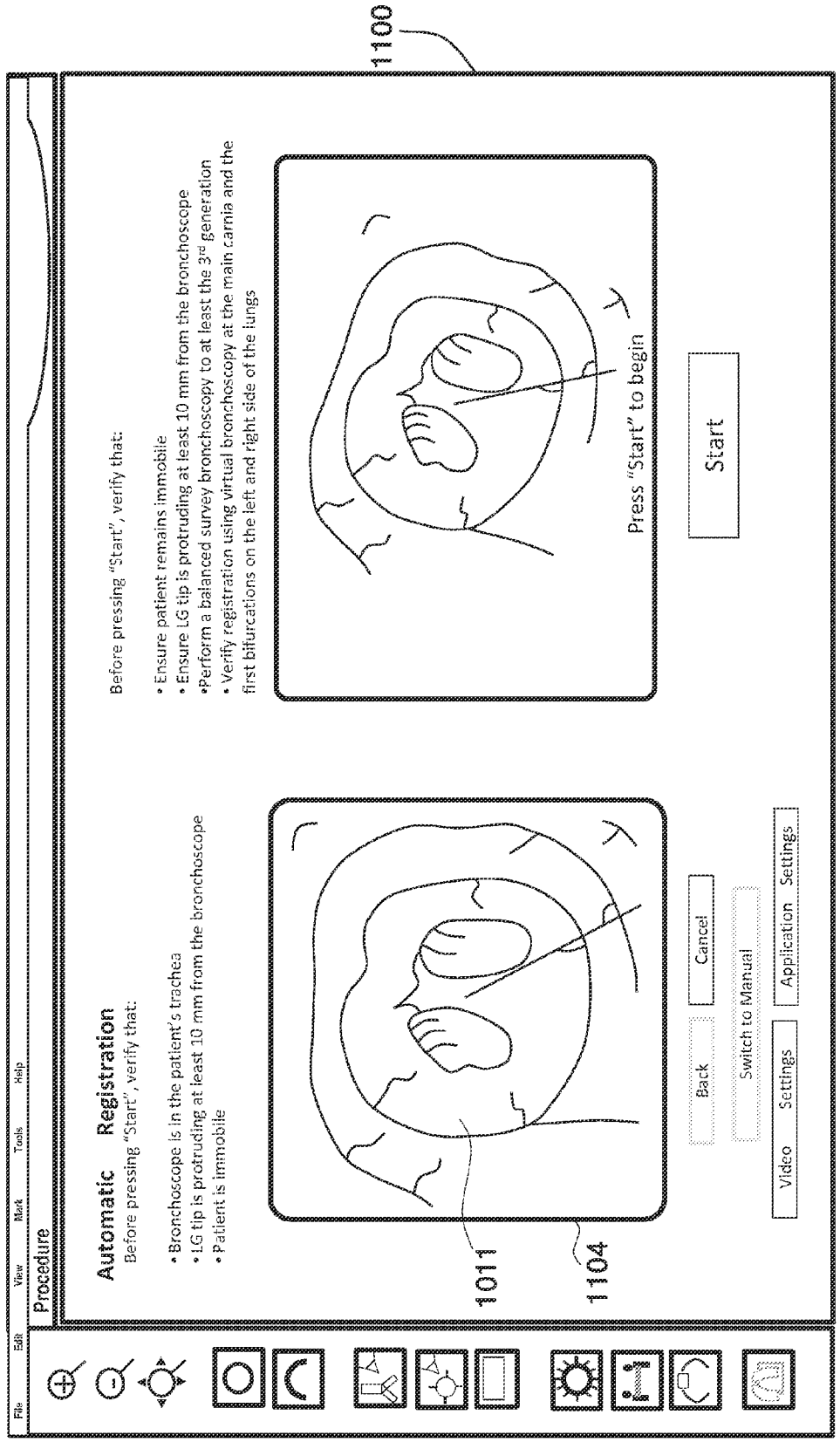
FIG. 15 is a screen shot of a CT based luminal navigation system in accordance with an embodiment of the present disclosure.

Yet a further procedure is described with reference to FIG. 15. In the method of FIG. 15 the bronchoscope 1004 is inserted into the patient 1000, as shown in FIG. 11. The locatable guide 1032 is extended beyond the end of the sheath 1040, both of which extend approximately 10 mm past the distal end of the bronchoscope 1004.

Once in place in the patient 1000, a screen 1100 will be displayed by the software on the monitoring equipment 1006 (FIG. 11). The right image is the actual bronchoscopic image 1102 generated by the bronchoscope 1004. Initially there is no image displayed in the left image 1104, this will be a virtual bronchoscopy, as discussed above, generated from the CT image data, once registration is complete.

Starting with the locatable guide 1036, and specifically the sensor element 1044 approximately 3-4 cm above the main carina, as viewed through the bronchoscope 1004, the bronchoscope is advanced into both the right and left lungs to the fourth generation of the lung passages. By traversing these segments of the lungs, sufficient data is collected as described above such that registration can be accomplished. When registration is achieved, which may be indicated to the user by highlighting the virtual bronchoscopy image 1104 in green, or some other visual indicator, the registration can be checked. This is accomplished by again directing the bronchoscope to image the main carina and both of the right upper lobe and left upper lobe carina. Visual comparison by the user confirms that the registration is accurate. If needed, rotation of the visual bronchoscopy by the user can correct minor image issues. If the user is displeased with the results, or is unable to achieve registration, perhaps due to a prior resection or treatment of the patient's lungs, manual registration is always available for use, as described above.

Now that the targets have been identified, the pathway planned, the bronchoscope 1004 including locatable guide 1032 inserted into the patient 1000, and the virtual bronchoscopy image registered with the image data of the bronchoscope 1004, the system is ready to navigate the location sensor 1044 to the target within the patient's lungs. The computer 1024 provides a display similar to that shown in FIG. 10 identifying the target 1017 and depicting the virtual bronchoscopy image 1011. However, appearing in each of the images on the display is the pathway from the current location of the location sensor 1044 to the target 1017. This is the pathway that was established during the pathway planning phase discussed above. The pathway may be represented, for example, by a colored line. Also appearing in each image is a representation of the distal tip of the locatable guide 1032 and location sensor 1044. By advancing the locatable guide 1032 and following the pathway the medical professional is able to follow the identified pathway to the target 1017. At times, as discussed above, the virtual bronchoscopy image 1017 may not provide sufficient accuracy, particularly at the pleura boundaries of the lungs. In such instances the user can rely on the CT images 1005-1009 to provide greater details. Though shown with just three views in images 1005-1009, there are in fact a wide variety of images that can be employed here, mostly derived from the CT imaging data.

Although the position of the location sensor 1044 is measured in real time, the target 1017 location is not. The target 1017 is generally considered fixed relative to the patient's body position 1000 which is monitored in real time by sensors 1020 (FIG. 12). However, navigation accuracy may decrease as a result of cyclic chest movement resulting from breathing. Preferably, precautions are taken to reduce the effects of this cyclic movement including reducing the respiration rate of the patient. In addition this movement may be accounted for in the software by sampling the position sensors positions 1020 selectively so that measurements are only made at an extreme of a cyclic motion. The extremes of the motion of the patient's chest can readily be identified by the cyclic displacement of sensors 1020 during the breathing cycle. It may be preferred to use the maximum exhalation state for measurements since this state typically remains steady for a relatively larger proportion of the breath cycle than the maximum inhalation state. Alternatively, measurements can be taken continuously, and the cyclic variations eliminated or reduced by additional processing. This processing may include applying a low-frequency filter to the measurements. Alternatively, an average of the measurements over a time period of the cyclic motion may be calculated and used to assist in approximating the location of the target. This is assisted by knowing whether the CT data was derived with the patient in a fully inhaled or exhaled position, which can be used for comparison and greater approximation of positioning.

Once the locatable guide 1032 has successfully been navigated to the target 1017 location, the locatable guide 1032 is preferably removed, leaving sheath 1040 in place as a guide channel for bringing a tool to the target location 1017. The medical tools may be biopsy tools that can be used to sample the target 1017. These samples are retrieved and a determination is made whether treatment of the target is necessary. Details of this system are included in U.S. Pat. No. 7,233,820, already incorporated herein by reference.

A further use of the sheath 1040 following removal of the locatable guide 1032 is as a conduit for the placement of one or more markers (1300 FIG. 17) within the patient. These markers can be used for a variety of purposes including identifying tumors and lesions for follow-up analysis and monitoring, to identify locations that biopsy sampling has been undertaken, and to identify the boundaries or he center of a tumor or lesion for application of treatment. Other uses will be understood by those of skill in the art as falling within the scope of the present disclosure.

The placement of markers can be particularly useful in the context of performing a video assisted thoracoscopic surgery (VATS) lung procedure. VATS procedures performed on a patient 1000 of FIG. 16A involves inserting a video scope 1200 (camera) and laparoscopic tools including a forceps 1202 and an ablation probe 1204 into the chest cavity of the patient 1000 though one or more ports formed in the chest wall. The video scope 1200 allows the surgeon to visualize the lung 1206 on a monitor 1208, as depicted in FIG. 16B. The ablation probe 1204 is inserted into the tissue of the lung 1206 and energized in order to ablate the tissue of interest and treat the lung tissue as described above.

Though described here with respect to treatment of lung tissue embodiments of the present disclosure are equally applicable for use in treatment of other tissues. For example, it is contemplated that the systems and methods of the present disclosure may be used to treat liver tissue, kidney tissue, pancreatic tissue, gastrointestinal tissue, interstitial masses, and other portions of the body known to those of skill in the art to be treatable via microwave ablation.

Returning to the treatment of lung tissue, lung lesions, especially small ones or those located on closer to the pleura boundaries are difficult for thoracic medical professionals to identify and treat visually. To most clearly distinguish the tissue of interest, the medical professional should have either a tactile or a visible marker placed near the tissue of interest to help target the tissue slated for removal or ablation.

Accordingly to one embodiment of the present disclosure, using the system described above with reference to FIGS. 11 and 12, a medical professional is able to navigate a sheath 1040 through the working channel of a bronchoscope 1004 by manipulating control handle 1038 and therewith locatable guide 1032 to position a sensor 1044 proximal tissue of interest. This navigation of the lung must be performed while the lungs are inflated, or at least undergoing normal, albeit slowed respiration by the patient. According to at least one embodiment, with the sheath 1040 remaining in place, the locatable guide 1032 is removed from the sheath 1040, the medical professional is able to use the sheath 1044 to deploy one or more markers to identify the location of interest. As noted, above, this may be in order to return to this location for further study, treatment, biopsy, etc., or this may be used to identify locations for VATS procedures.

Though described herein with respect to a particular planning and navigation systems, other pathway planning and navigation systems may be employed without departing from the scope of the present disclosure. For example, the systems described in commonly assigned U.S. patent application Ser. Nos. 13/477,279; 13/477,291; 13/477,374; 13/477,395; 13/477,406; and 13/477,417, the entire contents of which are incorporated herein by reference, as well as those systems described for example is U.S. Pat. No. 7,876,942 currently assigned to Activiewes, LTD.

In order to perform VATS procedures, following placement of the markers the lung 1206, or a portion of the lung 1206 is typically deflated. Deflation makes room for the video scope 1206 and other necessary tools (e.g., forceps 1202). Further, this deflation leads greater energy absorption during microwave ablation because of the lower dielectric constant and dissipation factor of air as compared to lung tissue, accordingly removal of the air increase the overall absorption of microwave energy by the lung tissue, leading to higher tissue temperatures. Additionally, deflation reduces the thermal cooling which would otherwise occur from respiration of the lung, further increasing thermal ablation effectiveness.

A variety of techniques for identification of the location of implanted markers can be employed including fluoroscopy, ultrasound, and other imaging modalities. These are particularly useful when the marker is equipped with a radio-opaque portion, formed of, for example, gold. VATS procedures in particular lend themselves to visual identification, particularly when performing treatment of tissues near the pleura boundaries of the lungs. Some techniques to improve visualization involve the injection of inks or dyes into the patient to identify the location of the marker. These techniques tend to be more of a clinician based ad hoc solution to visual identification.

As an initial matter visualizing of markers of any kind, especially in a discolored and diseased lung tissue, can be very difficult. Further, traditional dyes and solutions tend to be spread too broadly for accurate identification of the tissue to be identified, particularly if the marker is placed more than a few hours before the surgical procedure. Typically surgery must be undertaken within 72 hours of dye injection. Gold fiducial markers on the other hand are difficult if not impossible to identify without some imaging modality, and sometimes currently available fiducial markers tend to migrate over time, or even as a result of a patient cough.

One embodiment of the present disclosure is directed to placement of a marker using the system described herein to promote visual identification of the tissue of interest during VATS and so that the tissue can be percutaneously ablated using the microwave system of FIG. 2A. FIG. 17 shows such a marker 1300. The marker 1300 of FIG. 17 is made of made of a biocompatible material and includes an expanding material such as an implant grade hydrogel. In its dehydrated state, depicted in FIG. 18 as the darker cylinder 1302, the marker 1300 is compatible with and fits within the inner diameter of a sheath 1040 of the catheter assembly 1030 of FIG. 12. For example, the diameter of the marker 1300 in its dehydrated state may be approximately 2 mm.

One method of deployment is to use a push catheter (not shown) to force the marker 1300 through the sheath 1040. Markings on the push catheter enable the medical professional to know when the marker 1300 has been deployed out the distal end of the sheath 1040. Placement of the marker 1300 may be either into the airway directly or alternatively, into a void created using a biopsy tool. The void may be in for example a tumor or mass and may allow for clear identification of the center of the tumor for ablation purposes.

The color of the dark cylinder 1302 is due to the expanding material enclosed therein having absorbed an ink material, such as methelyne blue, indigo carmine, isosulfan blue, gentian violet, or others known to those of skill in the art. In one alternative, rather than an ink a radio opaque fluid/gel may also be employed.

Once placed in the body, the expanding material, such as a hydrogel, absorbs water and begins to expand until achieving an expanded size 1304. Similar technologies are currently employed for placing breast biopsy markers. Over a short period of time the expanding material swells which assists in securing the marker 1300 in place. According to the present disclosure, in addition to the foregoing, while fluid is being absorbed into the hydrogel, the ink in the hydrogel can begin to leave the hydrogel via osmosis. However, because of the hydrogel material the rate of osmosis of the ink is metered, such that migration of the ink is greatly reduced as compared to direct injection of the inks as discussed above. One advantage of using ink is that it has the ability to penetrate calcified lesions or surrounding parenchyma of the lung 1206 and to clearly identify its location to a surgeon when viewing the lungs through a video scope 1200, as shown in FIG. 16B.

Figure 18:
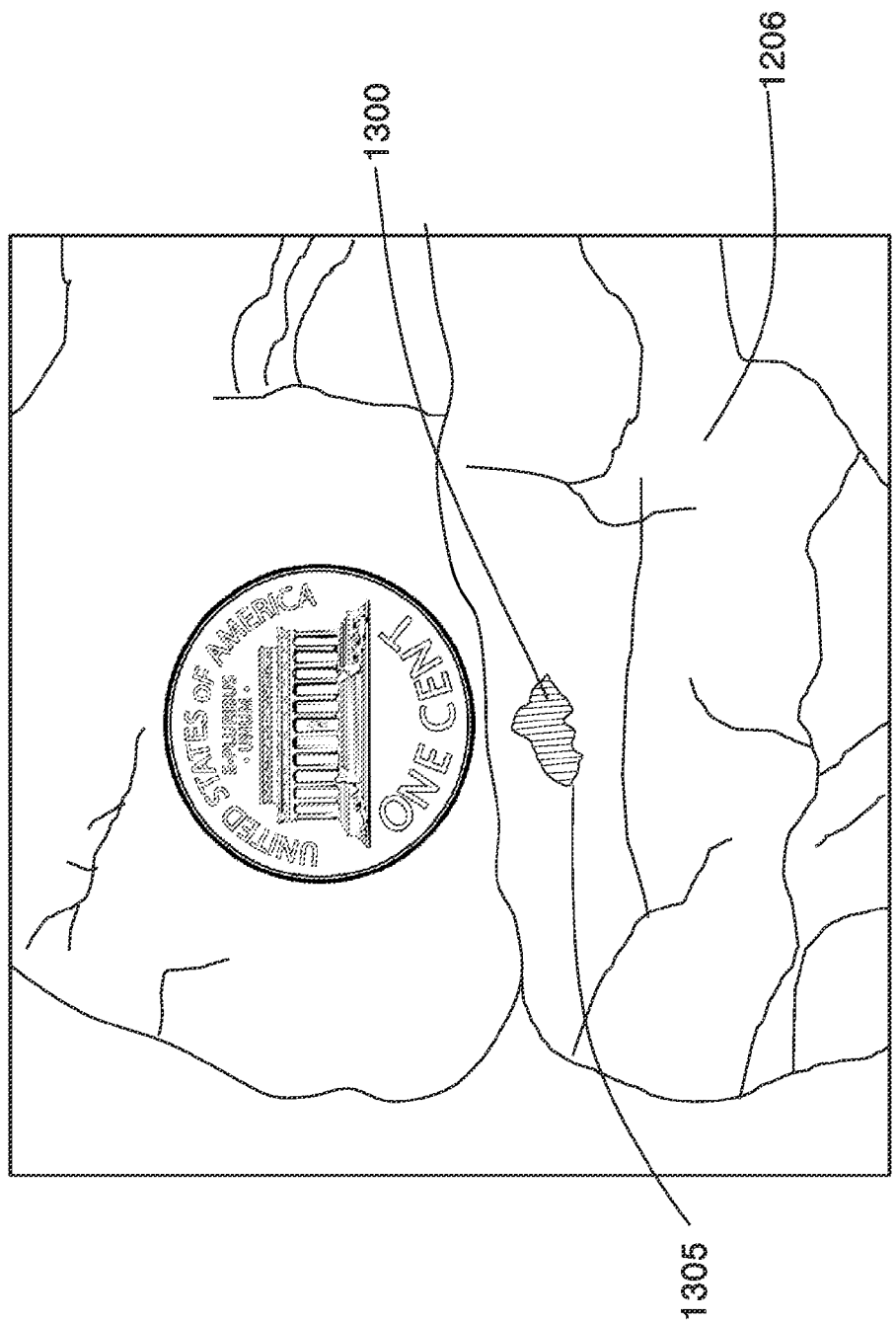
FIG. 18 is a perspective view of lung tissue having the marker of FIG. 17 implanted therein.
Figure 19:
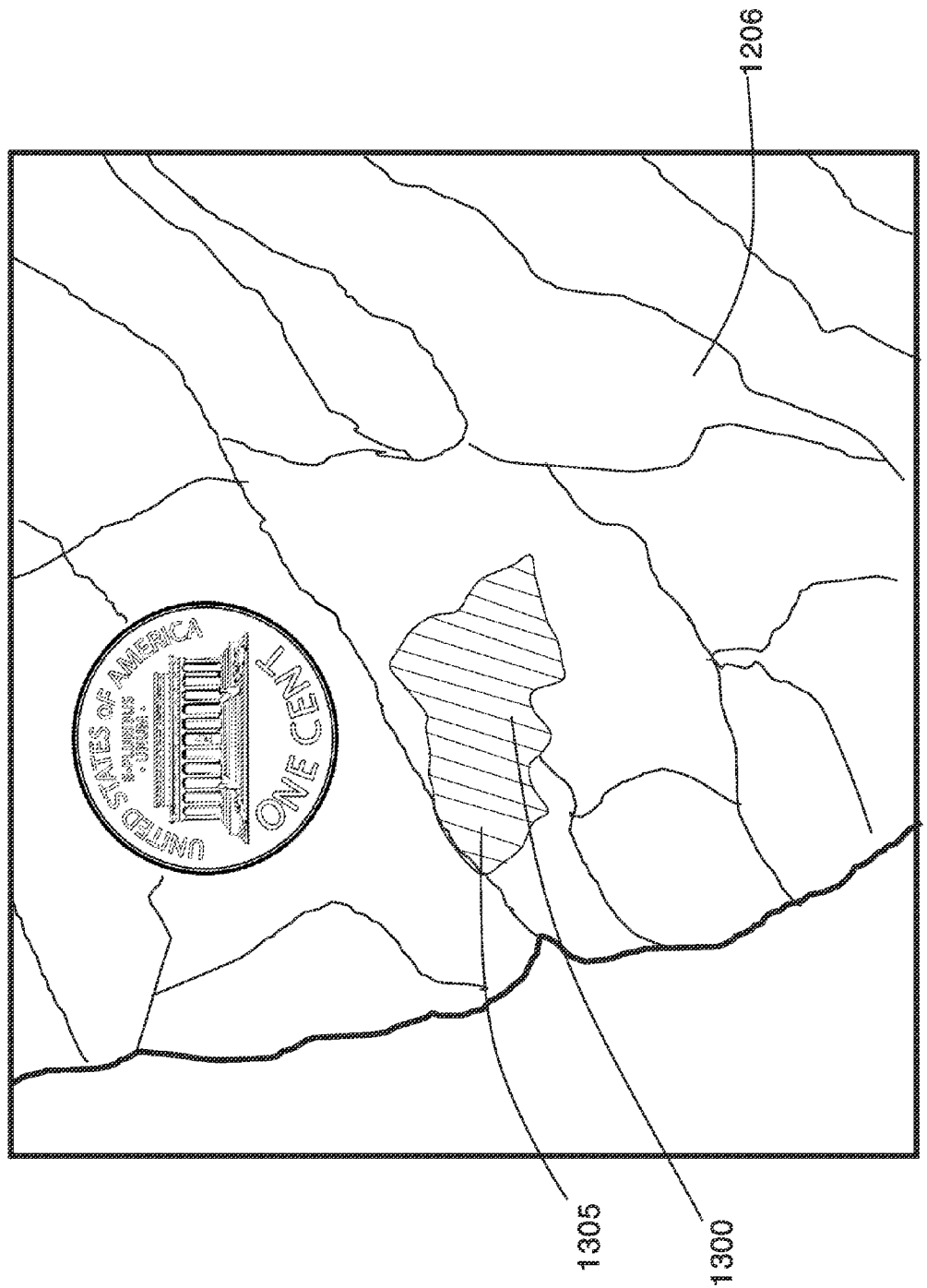
FIG. 19 is a perspective view of the marker of FIG. 18 at a some time after implantation.

FIG. 18 depicts the effect of the implantation of a marker 1300 in a lung 1206 according to the present disclosure. Specifically FIG. 18 provides the image a medical professional might see when viewing lung 1206 though a video scope 1200. The dime is placed in the image for size comparison purposes. This image is as one might see shortly (approximately 1-hour) after implantation, of marker 1300 near the pleura boundary of a lung 1206. FIG. 19 depicts the same marker 1300 approximately 16 hours after implantation in the lung 1206 and while the lung 1206 is in a deflated state. As can be seen by the comparison the ink 1305 in the marker 1300 clearly defines the location of the marker 1300 on the lung 1206, but has not diffused to the point of marking too much of the lung 1206, and thus provides a good indication of the location of the marker 1300. Thus the tissue of interest can be readily visualized by a medical professional performing a VATS procedure, for example to perform microwave ablation as disclosed herein. Further, as a result of the use of the marker 1300, even a small area of interest can be identified and a biopsy sample taken or surgical procedure undertaken and trauma to surrounding, otherwise healthy tissue can be minimized. Though shown above after 16 hours of implantation, it is contemplated that markers of the present disclosure can be implanted up to one week prior to the procedure and still provide useable identification of the tissue of interest.

Figure 20:
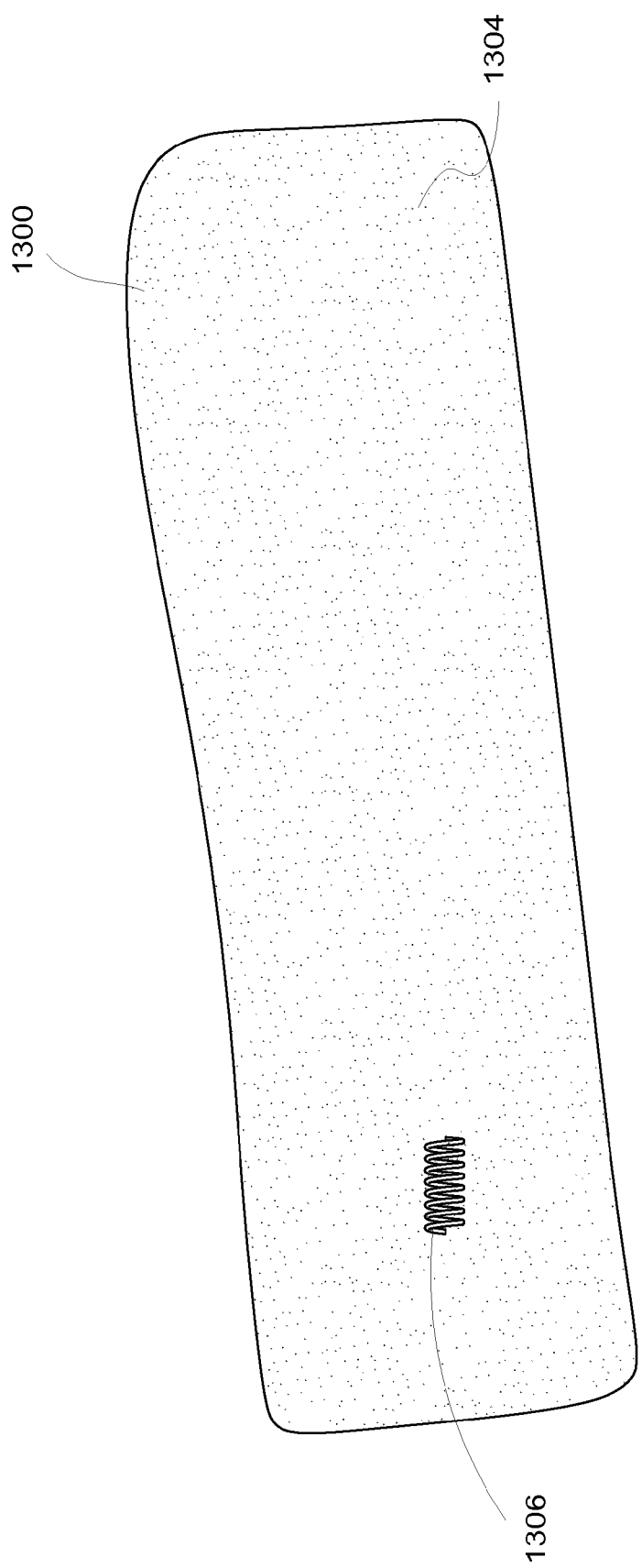
FIG. 20 is a perspective view of a marker in accordance with an embodiment of the present disclosure.

Another aspect of the marker of the present disclosure is that it may optionally contain a metallic or radio opaque marker within it. Metals usable for such a configuration include titanium, gold, and others. As shown in FIG. 20, the marker 1300 is depicted in its expanded state 1304, but without ink 1305, encloses a metallic (radio opaque) marker 1306. This metallic marker 1306 allows the position of the marker 1300 to be determined using fluoroscopy or other imaging modalities, to assist the surgeon. In the embodiments disclosed herein, the expandable material is preferably biodegradable, thus over time, for example 4-6 weeks the expandable material will degrade and be absorbed by the body.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of manufacturing comprising:
providing a coaxial feedline including an inner conductor, an insulator circumscribing the inner conductor, and an outer conductor circumscribing the insulator;
applying a balun short circumferentially about the outer conductor of the coaxial feedline;
applying a dielectric material circumferentially about the outer conductor of the coaxial feedline and in contact with the balun short to form a balun;
extending a temperature sensor along the coaxial feedline such that the sensor contacts the balun short;
securing the temperature sensor to the coaxial feedline with a first heat shrink material;
securing the dielectric material, balun short, and temperature sensor in contact with each other and to the coaxial feedline using a second heat shrink material to make a microwave ablation device.

2. The method of claim 1, further comprising exposing a distal end of the dielectric material such that it is not covered with the second dielectric material.

3. The method of claim 1, further comprising applying an electrically conducting ink to the surface of the second heat shrink material facing the dielectric material and balun short.

4. The method of claim 1, further comprising removing a portion of the outer conductor of the coaxial feedline distal of the balun to expose a length of an insulator between the outer conductor and an inner conductor of the coaxial feedline and form a feedpoint.

5. The method of claim 4, wherein the portion of the outer conductor between the balun and the feed point forms a proximal radiating section.

6. The method of claim 1, further comprising removing a distal portion of the insulator between the inner and outer conductors to expose a distal portion of the inner conductor.

7. The method of claim 6, further comprising inserting the distal portion of the inner conductor into an electrically-conducting element, the electrically-conductive element forming a distal radiating section of the ablation device.

8. The method of claim 6, further comprising inserting a proximal end of the coaxial feedline into a transition, the transition connecting the coaxial feedline to a coaxial cable for connection to a microwave generator.

9. The method of claim 8, further comprising inserting the connected feedline into an inner tubular member, such that at least a portion of the distal radiating section extends beyond the distal end of the inner tubular member.

10. The method of claim 9, wherein a proximal portion of the inner tubular member is secured in a hub divider formed of an elastomeric material and having formed therein a substantially non elastic metal ring for securing the proximal portion of the inner tubular member within the hub divider.

11. The method of claim 10, further comprising inserting the connected feedline and inner tubular member into a hub, wherein the hub divider and the transition form there between a first chamber.

12. The method of claim 11, further comprising inserting an outer tubular member into a distal opening formed in a hub cap.

13. The method of claim 12, further comprising inserting the outer tubular member and hub cap over the inner tubular member in a co-luminal arrangement and into the hub forming a second chamber between the hub cap and hub divider.

14. The method of claim 13, further comprising placing the hub including inner and outer tubular members, feedline, and transition into a handle body.

15. The method of claim 14, wherein the handle body comprises two housing halves, which when brought together to form the handle body secure the hub including the inner tubular member, the outer tubular member, and transition into place using one or more alignment pins.

* * * * *